United States Patent [19]

Smith et al.

[11] Patent Number: 4,954,502
[45] Date of Patent: Sep. 4, 1990

[54] 1-INDOLYALKYL-4-(SUBSTITUTED-PYRIDINYL)PIPERAZINES

[75] Inventors: David W. Smith, Clinton; Frank D. Yocca, Madison; Joseph P. Yevich, Southington; Ronald J. Mattson, Meriden, all of Conn.

[73] Assignee: Bristol-Myers Squibb Company, New York, N.Y.

[21] Appl. No.: 338,253

[22] Filed: Apr. 14, 1989

Related U.S. Application Data

[63] Continuation-in-part of Ser. No. 204,845, Jun. 10, 1988, abandoned.

[51] Int. Cl.$^5$ .................. A61K 31/495; A61K 31/44; C07D 401/14
[52] U.S. Cl. ...................... 514/253; 544/349; 544/364
[58] Field of Search ................. 544/364, 349; 514/253

[56] References Cited

U.S. PATENT DOCUMENTS

| | | | |
|---|---|---|---|
| 3,188,313 | 6/1965 | Archer | 544/373 |
| 3,472,855 | 10/1969 | Archer | 544/360 |
| 3,562,278 | 2/1971 | Archer | 544/373 |
| 4,302,589 | 11/1981 | Fanshawe et al. | 544/373 |

OTHER PUBLICATIONS

Trubitsyna et al., Chem. Abst., 93-215274y, (1980).
Golubev et al., Chem. Abst., 95-7218x, (1981).
Lanzilotti et al., Chem. Abst., 92-76222u, (1980).

*Primary Examiner*—Cecilia Shen
*Attorney, Agent, or Firm*—Richard P. Ryan

[57] ABSTRACT

A series of 1,4-disubstituted piperazine derivatives comprised of indol-3-ylalkyl and substituted pyridin-2-yl substituent groups. These compounds are useful as antidepressant agents.

58 Claims, No Drawings

1-INDOLYALKYL-4-(SUBSTITUTED-PYRIDINYL)-PIPERAZINES

CROSS-REFERENCE TO RELATED APPLICATION

This is a continuation-in-part application of Ser. No. 07/204,845 filed June 10, 1988, now abandoned.

BACKGROUND OF THE INVENTION

This invention generally pertains to heterocyclic carbon compounds having drug and bio-affecting properties and to their preparation and use. In particular the invention is concerned with 1,4-disubstituted piperazine derivatives wherein one substituent is indol-3-yl-alkyl and the other is a substituted pyridin-2-yl moiety. These compounds possess a unique serotonergic profile that should make them useful in treatment of depression.

Archer disclosed a large series of CNS-depressant indolylalkylpiperazines in U.S. Pat. No. 3,188,313 which issued June 8, 1965. Among the large number of moieties listed for possible substituent selection on the 4-nitrogen atom of the piperazine ring was pyridyl (unsubstituted). In U.S. Pat. No. 3,562,278, issued Feb. 9, 1971, Archer claimed a series of 1-(indol-3-ylethyl)-4-substituted-piperazines having psychomotor depressant activity. Among the possible 4-substituents listed was pyridyl, again unsubstituted.

Of less relevance is U.S. Pat. No. 3,472,855, issued October 1969 to Archer, which discloses extension of the series to benz[g]indolyl moieties as replacements for indolyl.

Similarly less relevant is U.S. Pat. No. 4,302,589, issued November 1981 to Fanshawe, et al., which discloses a series of related compounds wherein indoline has replaced the indole moiety. These compounds were disclosed as having antipsychotic properties.

None of the aforementioned references disclose or suggest the 1-indolylalkyl-4-(substituted-pyridinyl)-piperazine derivatives and their antidepressant utility of the present invention.

SUMMARY AND DETAILED DESCRIPTION OF THE INVENTION

In its broadest aspect, the present invention is concerned with piperazinyl derivatives having useful antidepressant properties characterized by a compound of Formula I.

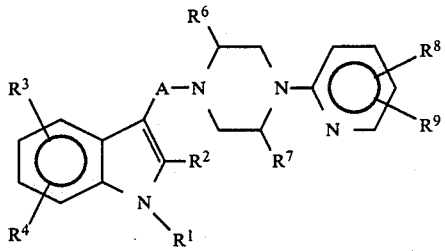

I

In Formula I; $R^1$ and $R^2$ are independently selected from hydrogen or lower alkyl. The descriptive term "lower" is used herein to denote an organic radical containing from 1 to 4 carbon atoms. The symbols $R^3$, $R^4$, $R^8$ and $R^9$ refer to moieties which are independently selected from among hydrogen, lower alkyl, lower alkoxy, carboxamide, halogen, trifluoromethyl, and lower alkylthio; with the proviso that both $R^8$ and $R^9$ cannot be hydrogen at the same time.

The symbol A represents a cycloalkanyl or cycloalkenyl ring comprised of from 5 to 7 carbon atoms. These bridging rings may be 1,2-; 1,3-; or 1,4-disubstituted bridging cycloalkanes or cycloalkenes. In the cycloalkenyl ring the double bond is adjacent to the point of attachment of the 3-indolyl ring. The symbol A can also be the structural fragment:

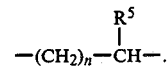

In this fragment linking the indole piperazine rings, n is an integer from 1 to 3 and $R^5$ can be either hydrogen or lower alkyl. The carbon atom to which $R^5$ is attached is adjacent to the piperazine ring.

Lastly, $R^6$ and $R^7$ are independently selected from hydrogen or methyl, or $R^6$ and $R^7$ can be taken together as a methylene bridge. Subclasses of compounds envisioned would be: A is cyclic or linear in structure; the piperazine ring is bridged or unbridged. Preferred classes of compounds are those wherein the indolyl and piperazinyl rings are connected by a 2 or 3 carbon linking chain and wherein $R^9$ is other than hydrogen and is attached to the 6-position of the 2-pyridinyl ring.

Additionally compounds of Formula I also encompass all pharmaceutically acceptable acid addition salts and/or solvates thereof. The present invention is also considered to include stereoisomers as well as optical isomers, e.g. mixtures of enantiomers as well as individual enantiomers and diastereomers, which arise as a consequence of structural asymmetry in certain compounds of the instant series. Separation of the individual isomers is accomplished by application of various methods which are well known to practitioners in the art.

It is to be understood that, as used herein, halogen denotes fluorine, chlorine, bromine and iodine; with the term "lower alkyl" referring to both straight and branched chain carbon radicals of from 1 to 4 carbon atoms inclusive. Illustrative of these radicals are carbon chains which can be methyl, ethyl, propyl, isopropyl, 1-butyl, 1-methylpropyl and 2-methylpropyl. Carboxamide intends a

radical.

The pharmaceutically acceptable acid addition salts of the invention are those in which the counter-ion does not contribute significantly to the toxicity or pharmacological activity of the salt and, as such, they are the pharmacological equivalents of the bases of Formula I. They are generally preferred for medical usage. In some instances, they have physical properties which makes them more desirable for pharmaceutical formulation such as solubility, lack of hygroscopicity, compressibility with respect to tablet formation and compatibility with other ingredients with which the substance may be used for pharmaceutical purposes. The salts are routinely made by admixture of a Formula I base with the selected acid preferably by contact in solution employing an excess of commonly used inert solvents such as water, ether, benzene, methanol, ethanol, ethyl acetate and acetonitrile. They may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from or retention on an ion exchange resin. Pharmaceutically acceptable acids for the purposes of salt formation of the substances of Formula I include sulfuric, phosphoric, hydrochloric, hydrobromic, hydroiodic, citric, acetic, benzoic, cinnamic, mandelic, phosphoric, nitric, mucic, isethionic, palmitic, heptanoic, and others.

The compounds of Formula I can be prepared by means of the processes shown in Scheme 1.

Scheme 1

Process #1

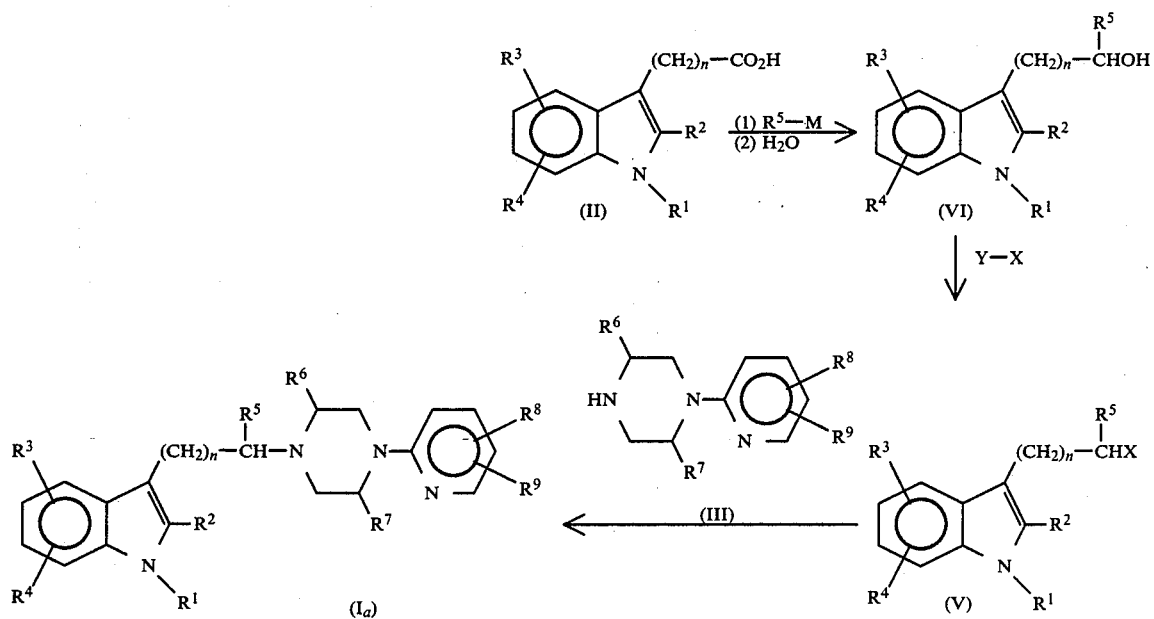

Process #2

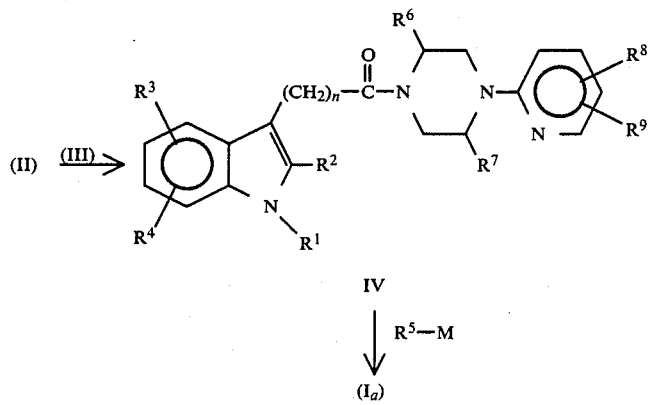

Process #3

-continued
Scheme 1
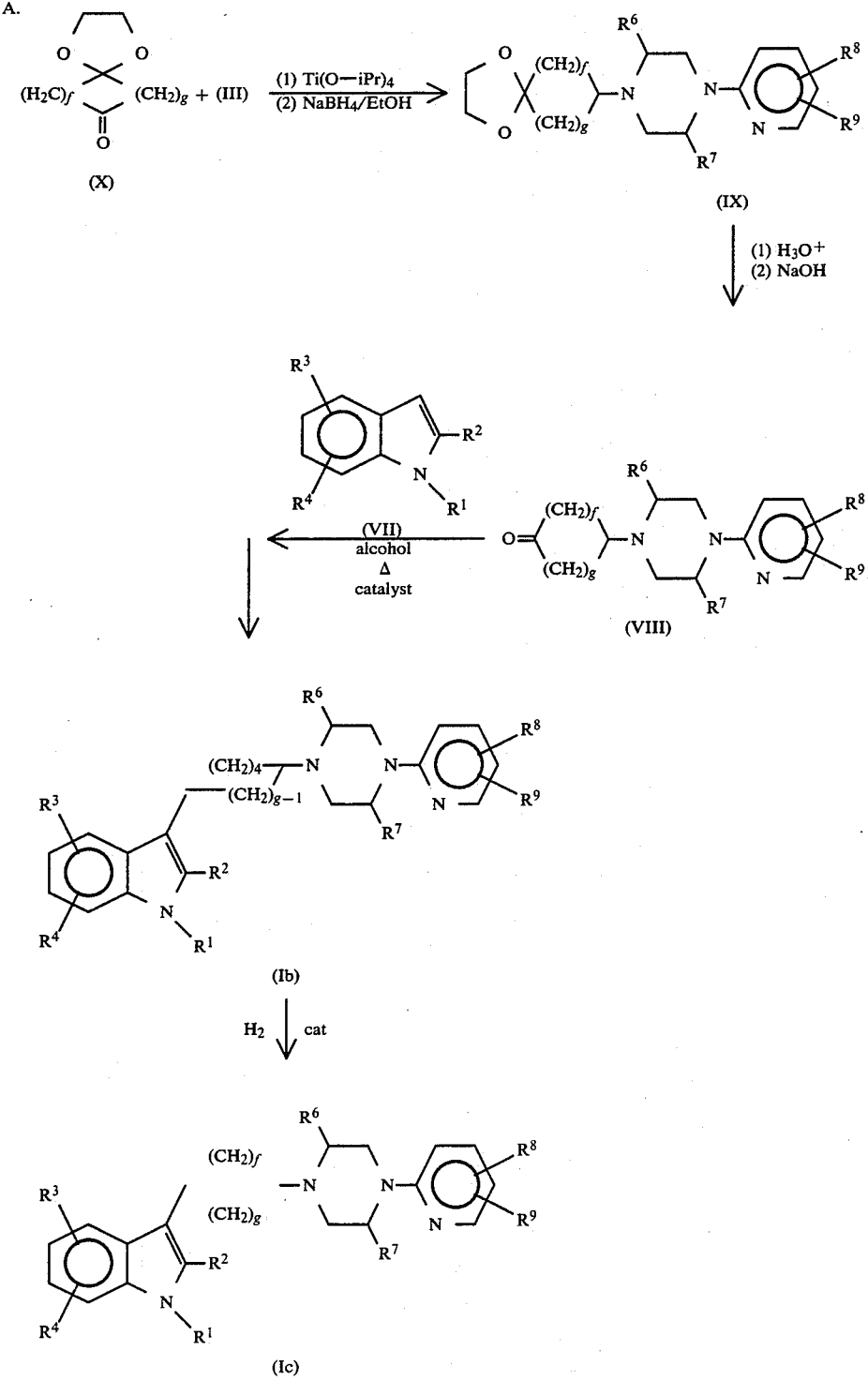

-continued
Scheme 1

B.

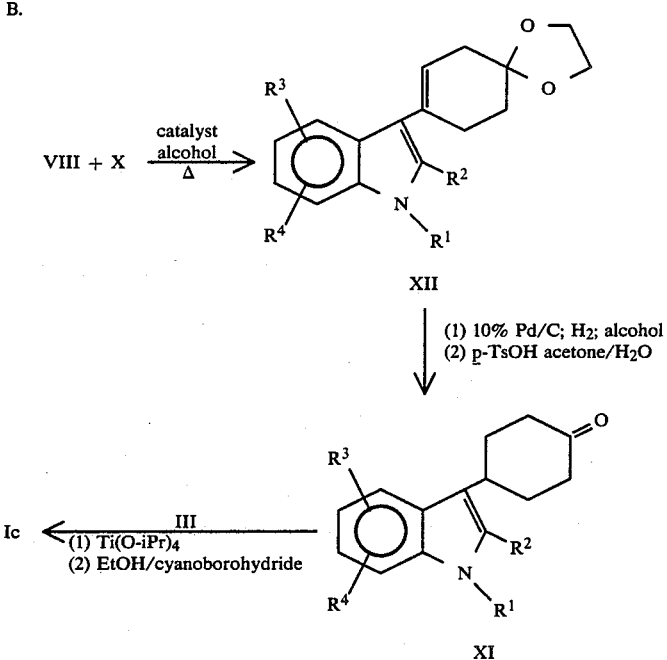

For the three processes depicted in Scheme 1; $R^1$ through $R^9$, and n are as defined hereinabove. Additional symbols appearing in Scheme 1 are f, g, M, X and Y. The symbols f and g are integers from 0 to 5 with the proviso that f+g must be equal to 3, 4 or 5. M represents a metalloid species such as magnesium, lithioaluminum, and the like; which, taken with $R^5$ are either hydride-type reducing agents such as lithium aluminum hyrides, diborane complexes, etc.; or organometallic alkylating agents such as Grignard reagents, etc. The reagent Y-X represents an organic leaving group reagent wherein X is the leaving group fragment such as tosyl, mesyl, halide, sulfate, phosphate and so forth; and Y is either a proton or a counter ion: e.g. XY can be HBr or tosyl chloride and the like. These reagents, symbolized by $R^5$-M and Y-X, as well as other reagent acronyms, are familiar to the practitioner skilled in organic synthesis and their structure and usage would be readily understood.

Process #1 in Scheme 1 comprises the following steps:

(1) Treatment of an indole carboxylic acid II with $R^5$-M, which is either a hyride reducing agent or alkylating agent depending on the selection of $R^5$ (hydrogen or lower alkyl). This results in generation of the indolylalkanol VI which is a secondary alcohol when $R^5$ is lower alkyl and a primary alcohol when $R^5$ is hydrogen (2) Conversion of the alcohol VI to an organic leaving group (also referred to as a nucleofuge in synthetic organic reaction terminology) by use of an appropriate Y-X reagent such as HBr or tosyl chloride to give intermediate V.

(3) Displacement of the leaving group anion by the nucleophilic pyridinylpiperazine III to provide the desired product of formula Ia.

Process #2 in Scheme 1 comprises a two-step reaction sequence:

(1) Condensation of the indolylcarboxylic acid II with the pyridinylpiperazine III, using standard condensation agents such as acid chlorides, acid anhydrides, dicyclohexylcarbodiimide, and the like, to afford the amide intermediate IV.

(2) Treatment of the amide IV with $R^5$-M to reductively alkylate or reduce to the desired formula Ia product.

Process #3 in Scheme 1 comprises the following sequence of steps:

A.

(1) The pyridinylpiperazine III is reductively alkylated with a cycloalkanedione mono-ethylene ketal X to give the ketal intermediate IX.

(2) Deprotecting the ketal IX to produce the cycloalkanone intermediate VIII.

(3) Condensing the cycloalkanone VIII with indole VII to yield the cycloalkenyl product Ib which can be catalytically reduced to the cycloalkanyl product Ic if desired.

B.

(1) The indole VII, cycloalkanedione mono-ethylene ketal X, and an acid or base catalyst (e.g. pyrrolidine) are refluxed in alcohol to give the condensation product XII.

(2) Intermediate XII is catalytically reduced to the saturated cycloalkane ketal which is deketalized to the cycloalkanone intermediate XI.

(3) Cycloalkanone XI is condensed with the pyridinylpiperazine III using conditions as shown to yield product Ic.

Reagents, solvents, and reaction conditions for the above described steps of the three processes would be known to one skilled in organic synthesis as all the steps comprise standard organic reactions, the details of which are readily available in the chemical literature. These processes may be adapted to variation in order to produce other compounds embraced by this invention but not specifically disclosed. Variations of the methods to produce the same compounds in somewhat different fashion will also be evident to one skilled in the art. As example of this, VI intermediate compounds wherein n is 1 are conveniently prepared by treating various substituted 3-indoleglyoxylic acid esters with LiAlH$_4$.

To provide greater descriptive detail, representative synthetic examples are provided hereinbelow in the "Description of Specific Embodiments" section. Similarly, preparations of starting intermediate compounds such as II and III, while readily available in the chemical literature, are also described using specific examples in that section of the patent specification.

The compounds comprising the present invention inhibit the re-uptake of endogenous serotonin. Selective inhibitors of serotonin uptake are effective for the treatment of mental depression and have been reported to be useful for treating chronic pain (see: R. W. Fuller, "Pharmocologic Modification of Serotonergic Function, Drugs for the Study and Treatment of Psychiatric and Other Disorders", *J. Clin. Psychiatry* 47:4 (Suppl.) April 1986, pp. 4–8). Compounds of the present invention are also envisioned to be useful in the following disorders: obsessive-compulsive disorder, feeding disorders, anxiety disorders and panic disorders.

Additionally, selected compounds of the invention potently inhibit norepinephrine re-uptake and blockade of endogenous norepinephrine re-uptake is also a mechanism through which it is believed that various antidepressant agents exert their therapeutic effect (see: "Antidepressants: Neurochemical, Behavioral, and Clinical Perspectives", edited by S. J. Enna, J. B. Malick and E. Richardson, (1981), Raven Press, New York, pp. 1–12).

Determination of endogenous monoaminergic re-uptake inhibition values both for serotonin and norepinephrine was accomplished using test methods described by P. Skolnick, et al.. *Br. J. Pharmacology* (1985), 86, pp. 637–644; with only minor modifications. In vitro IC$_{50}$ (nM) test values were determined for representative compounds of Formula I based on their inhibition of synaptosomal reuptake of tritiated serotonin. Test data IC$_{50}$ values lower than 500 nM are considered to reflect activity as an inhibitor of serotonin reuptake. Compounds with Ic$_{50}$ values lower than 100 nM comprise preferred compounds.

Another aspect of the instant invention provides a method for treating a mammal afflicted with depression or chronic pain which comprises administering systemically to said mammal a therapeutically effective amount of a compound of Formula I or a pharmaceutically acceptable acid addition salt thereof.

The administration and dosage regimen of compounds of Formula I is considered to be done in the same manner as for the reference compound fluoxetine, cf: Schatzberg, et al., *J. Clin. Psychopharmacology* 7/6 Suppl. (1987) pp. 44S–49S, and references therein. Although the dosage and dosage regimen must in each case be carefully adjusted, utilizing sound professional judgment and considering the age, weight and condition of the recipient, the route of administration and the nature and gravity of the illness, generally the daily dose will be from about 0.05 to about 10 mg/kg, preferably 0.1 to 2 mg/kg, when administered parenterally and from about 1 to about 50 mg/kg, preferably about 5 to 20 mg/kg, when administered orally. In some instances, a sufficient therapeutic effect can be obtained at lower doses while in others, larger doses will be required. Systemic administration refers to oral, rectal and parenteral (i.e. intramuscular, intravenous and subcutaneous). Generally it will be found that when a compound of the present invention is administered orally, a larger quantity of the active agent is required to produce the same effect as a similar quantity given parenterally. In accordance with good clinical practice, it is preferred to administer the instant compounds at a concentration level that will produce effective antidepressant effects without causing any harmful or untoward side effects.

The compounds of the present invention may be administered for antidepressant purposes either as individual therapeutic agents or as mixtures with other therapeutic agents Therapeutically, they are generally given as pharmaceutical compositions comprised of an antidepressant amount of a compound of Formula I or a pharmaceutically acceptable salt thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions.

The nature of the pharmaceutical composition employed will, of course, depend on the desired route of administration. For example, oral compositions may be in the form of tablets or capsules and may contain conventional excipients such as binding agents (e.g. starch) and we&:ting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection.

DESCRIPTION OF SPECIFIC EMBODIMENTS

The compounds which constitute this invention, their methods of preparation and their biologic actions will appear more fully from consideration of the following examples, which are given for the purpose of illustration only and are not be construed as limiting the invention in sphere or scope. In the following examples, used to illustrate the foregoing synthetic processes, temperatures are expressed in degrees Celsius and melting points are uncorrected. The nuclear magnetic resonances (NMR) spectral characteristics refer to chemical shifts ($\delta$) expressed as parts per million (ppm) versus tetramethylsilane (TMS) as reference standard. The relative area reported for the various shifts in the H NMR spectral data corresponds to the number of hydrogen atoms of a particular functional type in the molecule. The nature of the shifts as to multiplicity is reported as broad singlet (bs), singlet (s), multiplet (m) or doublet (d). Abbreviations employed are DMSO-d$_6$ (deuterodimethylsulfoxide), CDCl$_3$ (deuterochloroform) and are otherwise conventional. The infrared (IR) spectral descriptions include only absorption wave numbers (cm$^{-1}$) having functional group identification value. The IR determinations were employed using potassium bromide (KBr) as diluent. The elemental analyses are reported as percent by weight and are given in Table 3.

The following examples describe in detail the preparation of compounds of Formula I, as well as synthetic intermediates in each process. It will be apparent to those skilled in the art that modifications, both of materials and methods, will allow preparation of other compounds disclosed herein. From the foregoing description and the following examples it is believed that one skilled in the art is able to use the invention to the fullest extent.

A. Preparation of Intermediate Compounds

Some representative procedures for preparation of synthetic intermediate compounds utilized in the three processes of Scheme 1 are given hereinbelow. Most starting materials and certain intermediates (e.g. Formula II and VII compounds), are either commercially available or procedures for their synthesis are readily available in the chemical literature allowing their full utilization by one skilled in the art of organic synthetic chemistry.

Compounds of Formula III

EXAMPLE 1

1-(3-Methoxy-2-pyridinyl)piperazine

To a stirred mixture of 2-bromo-3-pyridinol (71.0 g) and pulverized KOH (77.8 g) in DMSO (500 mL) at 55°–60° C. and under $N_2$ atmosphere was added dropwise a solution of $CH_3I$ (72.4 g) in DMSO (100 mL). After the addition was complete, the reaction was maintained at 55°–60° C. for ½ h. The mixture was then poured into ice water (800 g) and the precipitate filtered. The precipitate was triturated with $Et_2O$ (3×500 mL) and the combined extracts treated in turn with 1 N NaOH (500 mL), water (500 mL), 1 N HCl (3×250 mL), and sat. NaCl solution (500 mL). The organic phase was dried with anhydrous $MgSO_4$, filtered, and concentrated under reduced pressure to afford 2-bromo-3-methoxypyridine (52.3 g; 68%).

Anhydrous piperazine (45.6 g) and 2-bromo-3-methoxypyridine (10.0 g) were heated neat in an autoclave at 100° C. for 20 h. Upon cooling, the mixture was treated with 5% $NaCO_3$ (20 mL) and extracted with $CH_2Cl_2$ (3×50 mL). The extracts were dried using anhydrous $K_2CO_3$, filtered, and concentrated under reduced pressure to yield 1-(3-methoxy-2pyridinyl)piperazine (III; 8.43 g; 82%) after silica gel chromatography ($CH_2Cl_2$/MeOH/$NH_4OH$; 93:7:0.7).

EXAMPLE 2

1-(3-Trifluoromethyl-2-pyridinyl)piperazine

A mixture of 2-chloro-3-trifluoromethyl pyridine (5.0 g), anhydrous piperazine (7.22 g), and micropulverized anhydrous $K_2CO_3$ (7.73 g) in acetonitrile (50 mL) was heated at reflux with stirring while under $N_2$ atmosphere for 20 h. The excess acetonitrile was removed under reduced pressure and water (15 mL) added to the concentrate. Ihe aqueous phase was extracted with $CH_2Cl_2$ (3×50 mL). The combined $CH_2Cl_2$ extracts were washed with sat. NaCl solution, dried with anhydrous $MgSO_4$, and concentrated under reduced pressure. Silica gel chromatography ($CH_2Cl_2$/MeOH/$NH_4OH$; 94:6:0.6) of the residue yielded 1-(3-trifluoromethyl-2pyridinyl)piperazine (III; 5.50 g; 85%).

EXAMPLE 3

1-(6-Methoxy-2-pvridinyl)piperazine

A mixture of 1-(6-chloro-2-pyridinyl)piperazine (6.0 g) and NaOMe (16.42 g) in DMF (25 mL,) was heated at 100° C. under nitrogen atmosphere for 20 h. The excess DMF was then removed under reduced pressure. Water (5 mL) was added to the residue and the mixture extracted with $CH_2Cl_2$. The combined organic layers were washed with sat. NaCl solution, dried with anhydrous $MgSO_4$, filtered and concentrated under reduced pressure. Silica gel chromatography ($CH_2Cl_2$/MeOH; 98:2) of the concentrate yielded the 4-(6-methoxy-2-pyridinyl)1-piperazinecarboxaldehyde (5.13 g; 81%).

A mixture of the formamide intermediate, prepared above, (3.55 g) in 6 N HCl (30 mL) was heated at reflux for ½ h. The reaction was cooled to 0° C., made basic with 10N NaOH, and extracted with $CH_2Cl_2$ (3×50 mL). The combined organic layers were washed with sat. NaCl solution, dried with anhydrous $K_2CO_3$, filtered, and concentrat.ed under reduced pressure to afford 1-(6-methoxy-2-pyridinyl)piperazine (2.72 g; 83%).

EXAMPLE 4

1-(6-Chloro-2-pyridinyl)piperazine

A mixture of 2.6-dichloropyridine (4.0 g), anhydrous piperazine (6.97 g), and micropulverized anhydrous $K_2CO_3$ (7.45 g) in acetonitrile (50 ml) was heated at reflux with stirring while under $N_2$ atmosphere for 20 h. The excess acetonitrile was removed under reduced pressure and water (15 mL) added to the concentrate. The aqueous phase was extracted with $CH_2Cl_2$ (3×50 mL). The combined $CH_2Cl_2$ extracts were washed with sat. NaCl solution, dried with anhydrous $MgSO_4$, are concentrated under reduced pressure. Silica gel chromatc,graphy ($CH_2Cl_2$/MeOH/$NH_4OH$; 94:6:0.6) of the residue yielded 1-(6-chloro-2-pyridinyl)piperazine (4.80 g; 90%).

EXAMPLE 5

2-(3-Methoxy-2-pyridinyl)-(1S,4S)-2,5-diazabicyclo[2.2.1]heptane

A. Preparation of (1S,4S)-N-Benzyl-2,5-diazabicyclo-[2.2.1]heptane (cf: J. Org. Chem. (1966), 31. 1059–1062)

(1) N-Tosylhydroxy-L-proline

To a solution of hydroxy-L-proline (80 g) in 2N NaOH (800 mL) was added tosyl chloride (136.1 g) in $Et_2O$ (700 mL). The reaction mixture was stirred at 0° C. for 1½ h and continued for an additional 3½ h at 23° C. The aqueous layer was separated, acidified with concentrated HCl to pH 1 and allowed to stand at −10° C. for 12 h. The precipitate was filtered, washed with cold water, and concentrated in vacuo to a volume of 300 mL. The precipitate obtained was combined with the previous precipitate. The combined solids were recrystallized from ethyl acetate. Drying in vacuo at 50° C. for 24 h afforded trans-4-hydroxy-1-(4-toluenesulfonyl)-L-proline (107.38 g, 62%).

(2) Potassium salt of trans-4-hydroxy-1-(4-toluenesulfonyl)-L-proline

To a solution of trans-4-hydroxy-1-(4-toluenesulfonyl)-L-proline (107.38 g) in acetone (450 mL) was added potassium 2-ethyl hexanoate in BuOH (1.91N; 189.5 mL). After standing at 23° C. for 20 min, the insoluble material was filtered and the resulting solution was concentrated to 320 mL. $Et_2O$ (1000 mL) was added to the concentrate and the solvents removed under reduced pressure yielting a solid (122.90 g). The hygrosoopic product was used in the next step without further purification.

(3) N-Tosylhydroxy-L-proline methyl ester

To a solution of potassium trans-4-hydroxy-1-(4-toluenesulfonyl)-L-proline (122.90 g) in 250 mL of N,N-dimethylacetamide was added methyl iodide (24.5 mL) while under nitrogen atmosphere. The light protected mixture was stirred 16 h. The mixture was poured onto ice water and extracted with $CH_2Cl_2$ (3×400 mL). The combined organic extracts were washed with 2% $NaHCO_3$ (400 mL), $H_2O$ (4×1.5 L), dried over $MgSO_4$, filtered, and concentrated under reduced pressure to leave a viscous oil. The crude oil was triturated within petroleum ether to give N-tosylhydroxy-L-proline methyl ester as a pale yellow solid (63.20 g, 56.2%) which was used in the next step without further purification.

(4) (2S,4R)-1-(4-toluenesulfonyl)-2-hydroxymethyl4-hydroxy pyrrolidine

To a solution of N-tosylhydroxy-L-proline methyl ester (62.20 g) in THF (600 mL) at 0° C. for 1 h and allowed to stand at 23° C. for 18 h. The reaction mixture was cooled to −20° C., made neutral with 6N HCl, and concentrated under reduced pressure. The residue was treated with water (550 mL) and extracted with EtOAc (4×300 mL). The combined organic extracts were washed with $H_2O$, dried over $MgSO_4$, filtered, and concentrated under reduced pressure to give N-tosylhydroxy-L-prolinol as a white solid (50.56 g, 88.8%) which was used in the next step without further purification.

(5) (2S,4R)-1-(4-toluenesulfonyl)-2-(4-toluenesulfonyloxymethyl)-4-(4-toluene-sulfonyloxy)-pyrrolidine To a solution of p-toluenesulfonyl chloride (155 g) in pyridine (330 mL) at 0° C. was added N-tosylhydroxy-L-prolinol (104.40 g). The reaction mixture was kept at 6° C. for 72 h and then poured into cold 2N HCl (2.5 L). The aqueous layer was extracted with $CH_2Cl_2$ (3×1000 mL). The combined organic extracts were dried over $MgSO_4$, filtered, and concentrated under reduced pressure to give an oil. The oil was triturated with EtOH and the solid that formed was collected by filtration. The crude product was recrystallized from EtOH (3.5 L) to give tritosylhydroxy-L-prolinol (99.87 g, 44.2%, m.p. 130°–132° C., $[\alpha]_D^{24} = -57.1$, c=1.2, acetone).

(6) 1S,4S)-2-(4-toluenesulfonyl)-5-phenylmethyl-2,5-diazabicyclo[2.2.1]heptane

To a suspension of tritosylhydroxy-L,-prolinol (98.87 g) in toluene (350 mL) was added benzylaxine (54.83 g). The resulting mixture was heated at reflux for 18 h and allowed to cool to 23° C. The reaction mixture was filtered and the solvent removed under reduced pressure. The residue was triturated with ethanol and the solid that formed was collected by filtration to give (1S,4S)2-(4-toluenesulfonyl)-5-phenylmethyl-2,5-diazabicycloheptane (54.18 g, 93.2%) which was used in the next step without further purification.

(7) (1S,4S)-N-benzyl-2,5-diazabicyclo[2.2.1]heptane dihydrobromide

A mixture of (1S,4S)-2-(4-toluenesulfonyl)-5-phenylmethyl-2,5-diazabicyclo[2.2.1]heptane (54.9 g) in acetic acid (830 mL) containing hydrobromic acid (30% wt) was heated at 70° C. for 18 h. The reaction mixture was allowed to cool and concentrated under reduced pressure to a final volumen of ca. 300 mL. The precipitate that formed was filtered and washed with acetone to give (1S,4S)-N-benzyl-2,5-diazabicyclo[2.2.1]heptane (50.30 g 91.3%, m.p. 272-275° C.).

By adjusting the starting materials and using the foregoing synthetic scheme the other isomer, (1R,4R)-N-benzyl-2,5-diazabicyclo[2.2.1]heptane can be obtained (cf: J. Org. Chem. (1981), 46 2954–2960).

B. 2-(3-methoxy-2-pyridinyl)-(1S,4S)-2,5-diazabicyclo[2.2.1]heptane (1) 2-(3-methoxy-2-pyridinyl)-5-phenylmethyl-(1S,4S)-2,5-diazabicyclo[2.2.1]-heptane A mixture of 2-bromo-3-methoxy pyridine (9.9 g) and (1S,4S)-N-benzyl-2,5-diazabicyclo[2.2.1]heptane (10.9 g) was heated at 100° C. in a Parr bomb for 67 h. The reaction mixture was cooled to 23° C., dissolved in $CH_2Cl_2$, extracted with 5% $NaHCO_3$, and finally with $H_2O$. The organic layer was dried over $K_2CO_3$, filtered, and concentrated under reduced pressure. The crude oil was purified by silica gel chromatography ($CH_2Cl_2$:MeOH; 96:4) to give the desired product (7.93 g, 51%).

(2) 2-(3-methoxy-2-pyridinyl)-5-phenylmethyl-(1S,4S)-2,5-diazabicyclo[2.2.1]heptane (7.88 g) in EtOH (250mL) was acidified to a pH of 1 with ethanolic HCl. The reaction mixture was treated with 5% palladium-on-carbon (2.05 g) and hydrogenated at 50 psi at 60° C. for 6 h. After this time, the heating was discontinued and the reaction mixture was allowed to cool to room temperature and the hydrogenation continued for 16 h. The reaction mixture was filtered through celite. The filtrate was concentrated under reduced pressure and the residue was made alkaline by the addition of 5N NaOH. The solution was extracted with $CH_2Cl_2$ (4×250 mL) and combined $CH_2Cl_2$ extracts were dried over $K_2CO_3$, filtered, and conoentrated under reduced pressure to give 2-(3-methoxy-2pyridinyl)-(1S,4S)-2,5-diazabicyclo[2.2.1-]heptane (4.67 g; 85.2%).

Compounds of Formula IV

EXAMPLE 6

1-[4-(1H-indol-3-yl)-1-oxobutyl]4-(3-methoxy-2-pyridinyl)piperazine

To a mixture of 1-(3-methoxy-2-pyridinyl)piperazine (III; 1.28 g), 3-indolebutyric acid (1.08 g), and triethylamine (1.02 g) in $CH_2Cl_2$ (50 mL) was added 1-methyl-2-chloropyridinium iodide (1.62 g). The reaction was heated at reflux with stirring and under $N_2$ atmosphere for 4 h. After cooling to ambient temperature, the solution was extracted with aqueous 5% HCl followed by aqueous 5% $NaHCO_3$. The organic phase was dried with anhydrous $K_2CO_3$, filtered, and concentrated under reduced pressure. Silica gel chromatography ($CH_2Cl_2$/MeOH; 98.2) of the concentrate afforded the amide product (IV; 1.00 g; 50%).

Compounds of Formula V

EXAMPLE 7

3-(3-bromopropyl)-1H-indole

Phosphorus tribromide (17.4 g) in $Et_2O$ (30 mL) was added dropwise to a Et20 solution (100 mL) containing 3-(3-hydroxypropyl)indole (VI; 7.5 g) at 0° C. with stirring and under $N_2$ atmosphere. After the addition was complete, the reaction was allowed to warm to 23° C. and continuously stirred for 16 h. At the end of this time, the reaction was cooled to 0° C. and ice (ca. 25 mL) added portionwise and stirred an additional 2 h. The organic phase was separated from the aqueous phase and the aqueous layer extracted with $Et_2O$. The combined organic phases were washed with sat. NaCl solution, dried with $MgSO_4$, filtered and concentrated under reduced pressure to afford 3-(3-bromopropyl)indole (V; 1.51 g; 15%).

EXAMPLE 8

5-Fluoro-3-(2-bromoethyl)indole

To a solution of 5-fluoro-3-(2-hydroxyethyl)indole (10.3 g, 0.056 mol) and CBr (24.8 g, 0.073 mol) in 100 mL of dry acetonitrile at 0° C. under Ar was added a solution of triphenylphosphine (19.6 g, 0.073 mol) in 200 mL of dry acetonitrile. The mixture was stirred at 0° C. for 1 h and then at room temperature for 2 h. The resulting mixture was evaporated and the residue was chromatographed (SiO$_2$/ethyl acetate-hexane=1:4) to give the product (8.50 g, 61%) as a brown solid;

IR (neat) 3440 cm$^{-1}$;

$^1$Hnmr (80 MHz, CDCl$_3$)

δ:7.75 (br s, 1H), 7.15–6.57 (m, 4H), 3.53–3.32 (m, 2H), 3.17–2.94 (m,2H).

Compounds of Formula VI

EXAMPLE 9

3-(3-hydroxypropyl)-1H-indole

To a stirred suspension of LiAlH$_4$ (4.02 g) in THF (200 mL) at 0° C. and under N atmosphere was added dropwise a THF solution (100 mL) containing indole-3-propanoic acid (20.0 g). After the addition was complete, the reaction was heated at reflux for 16 h, after which time the mixture was cooled to 0° C. and water (4 mL) added, followed by 15% NaOH (4 mL), and finally additional water (12 mL). The reaction was filtered and the THF filtrate extracted with 5% NaOH (4 mL), and finally additional water (12 mL). The reaction was filtered and the THF filtrate extracted with 5% NaHCO$_3$ followed by a sat. NaCl solution. The organic phase was dried with anhydrous K$_2$CO$_3$, filtered, and concentrated under reduced pressure to yield 3-(3-hydroxypropyl)indole (VI; 7.5 g; 41%).

EXAMPLE 10

3-(2-hydroxyethyl)-1H-indole

To a stirred suspension of LiAlH$_4$ (3.24g) in THF (200 mL) at 0° C. and under N$_2$ atmosphere was added tropwise a THF solution (50 mL) containing indole-3-acetic acid (10.0 g). After the addition was complete, the reaction was heated at reflux for 3 h, after which time the mixture was cooled to 0° C. and water (3.3 mL) added, followed by 15% NaOH (3.3 mL), and finally additional water (9.9 mL). The reaction was filtered and the filter cake washed with Et$_2$O. The organic layers were combined, dried with anhydrous MgSO$_4$, filtered, and concentrated under reduced pressure to yield 3-(2hydroxyethyl)indole (VI; 7.4 g; 80%).

EXAMPLE 11

5-Floro-3-(2-hydroxyethyl)indole

To a suspension of LiAlH$_4$ (8.60 g, 0.23 mol) in 400 mL of dry THF was added 5-fluoro-3-indoleglyoxylic acid ethyl ester (13.50 g, 0.057 mol) portionwise at room temperature. Preparation of this ester intermediate is given hereinbelow. The mixture was heated to reflux under Ar for 1 h and was then cooled to 0° C. and quenched according to the method of Fieser (Fieser and Fieser, "Reagents for Organic Synthesis", Vol. 1, pg. 584). The resulting slurry was filtered and the filter cake was washed with THF. The filtrate was dried (Na$_2$SO$_4$) and evaporated to give the product (10.00 g, 100%) as a yellow oil. It was used as such without further purification;

IR (neat) 3420 cm$^{-1}$ $^1$Hnmr (80 MHz, CDCl$_3$)

δ7.73 (br s, 1H), 7.1–6.4 (m, 4H), 3.57 (t, J=8 Hz, 2H), 2.66 (t, J=8 Hz, 2H), 1.20 (br s, 1H).

5-Fluoro-3-indoleglyoxylic acid ethyl ester

To a solution of 5-fluoroindole (7.35 g, 0.054 mol) in 75 mL of anhydrous ether was added oxalyl chloride (5.60 mL, 0.064 mol) dropwise at 0° C. under Ar.

The yellow suspension was stirred at 0° C. for 1½ h and then the solid was collected by filtration and dried in vacuo to give 5-fluoro-3-indoleglyoxylyl chloride (12.0 g, 100%) as a yellow solid; IR (neat) 1765, 1627 cm$^{-1}$.

This solid was taken up in 160 mL of absolute ethanol and was then treated with triethylamine (8.1 mL, 0.058 mol) dropwise at 0° C. under Ar. The mixture was refluxed for 4½ h and was then allowed to cool to room temperature. The resulting precipitate was filtered and then dried in vacuo to give the product (10.8 g, 87%) as a yellow solid which was used without further purification.

Compounds of Formula VIII

EXAMPLE 12

4-[4-(6-Chloro-2-pyridinyl)-1-piperazinyl]-cyclohexan-1-one

A solution of 4-[4-(6-chloro-2-pyridinyl)-1-piperazinyl]-cyclohexan-1-one ethylene ketal (IX, Example 13: 7.56 g, 22 mmole) in 10% aqueous HCl (200 mL) was refluxed for 16 h. The solution was cooled and then neutralized with 30% aqueous NaOH solution. The mixture was then extracted with ethyl acetate (3×75 mL) and the extracts were dried over Na$_2$CO$_3$. The mixture was filtered and the filtrate was concentrated in vacuo. The residue was chromatographed on silica gel using ethyl acetate as the eluent to give the desired ketone product (VIII) as an oil (5.70 g, 92%).

Compounds of Formula IX

EXAMPLE 13

4-[4-(6-Chloro-2-pyridinyl)-1-piperazinyl]-cyclohexan-1-one ethylene ketal

A solution of 1-(6-chloro-2-pyridinyl)-piperazine (8.00 g, 40 mmole) 1,4-cyclohexanedione mono-ethylene ketal (6 25 g, 40 mmole), and titanium(IV) isopropoxide (15 mL, 14.21 g, 50 mmole) was heated to 80° C. for 30 min. The mixture was cooled and diluted with absolute ethanol (40 mL). Sodium borohydride (ten 0.4 g tablets, 0.1 mole) was added and the mixture was stirred for 4 h. Water (10 mL) was added to the solution with stirring and the solid titanium dioxide was filtered off. The filtrate was concentrated in vacuo and the residue was dissolved in CH$_2$Cl$_2$ (75 mL). The solution was again filtered and the filtrate concentrated in vacuo. The residue was chromatographed on silica gel using ethyl acetate as the eluent to give the desired ketal product (IX) as an oil (7.56 g, 56%).

B. Preparation of Formula I Products

By Process 1 (Ia Products)

EXAMPLE 14

4-[6-Chloro-2-pyridinyl]-1-[2-(1H-indol-3-yl)-ethyl]piperazine hydrochloride A mixture of 3-(2-bromoethyl)indole (2.05 g), 1-(6-chloro-2-pyridinyl)piperazine (3.61 g), micropulverized K₂CO₃ (2 52 g) and tetrabutylammonium hydrogen sulfate (0.16 g) in acetonitrile (25 mL) was heated at reflux under N₂ atmosphere for 2½ h. The excess acetonitrile was removed under reduced pressure and water (15 mL) added to the concentrate. The aqueous phase was extracted with CH₂Cl₂ (3×50 mL). The combined CH₂Cl₂ extracts were washed with sat. NaCl solution, dried with anhydrous K₂Cl₃, and concentrated under reduced pressure. Silica gel chromatography (EtOAc/Hexanes; 70:30) of the residue yielded the free base (3.10 g; 99%) which was treated with ethanolic HCl to provide the desired Ia product (2.63 g; 77%).

Anal. Calcd. for $C_{19}H_{21}N_4Cl.HCl$:

C, 60.49; H, 5.88; H, 14.85 found: C, 60.27; H, 5.88; N, 14.66

NMR (DMSO-d₆): 3.24 (8H, m); 3.72 (2H, m); 4.40 (2H, m); 6.81 (1, d, 7.4 Hz); 7.02 (3H, m); 7.25 (lH, d, 1.0 Hz); 7.39 (1H, m); 7.64 (2H, m); 10.85 (1H, bs); 10.98 (lH, bs).

IR (KBr): 750, 770, 960, 1140, 1270, 1420, 1460, 1550, 1600, 2440 and 3240 cm⁻¹.

EXAMPLE 15

1-[2-(1H-indol-3-yl)-ethyl]-4-6-trifluoromethyl-2-pyridinyl]piperazine hydrochloride A mixture of 3-(1-bromoethyl)indole (1.12 g), 1-(6-trifluoromethyl-2-pyridinyl)piperazine (2.31 g), micropulverized K₂CO₃ (1.38 g) and tetrabutylammonium hydrogen sulfate (0.08 g) in acetonitrile (50 mL) was heated at reflux under N₂ atmosphere for 2½ h. The excess acetonitrile was removed under reduced pressure and water (10 mL) added to the concentrate. The aqueous phase was extracted with CH₂Cl₂ (3×50 mL). The combined CH₂Cl₂ extracts were washed with sat. NaCl solution, dried with anhydrous K₂CO₃, and concentrated under reduced preesure. Silica gel chromatography (CH₂Cl₂/MeOH; 98:2) of the residue yielded the free base (1.56 g; 83%) which was treated with ethanolic HCl to yield the hydrochloride salt of the desired Ia product (1.17 g; 68%).

Anal. Calcd. for $C_{20}H_{21}N_4F_3.HCl$:

C, 58 47; H, 5.40; N, 13.64

Found C, 58.37; H, 5.38; N, 13.56.

NMR (DMSO-d₆): 3.25 (8H, m); 3.72 (2H, d, 13.4 Hz); 4.48 (2H, d, 13.4 Hz); 7.10 (5H, m); 7.34 (1H, d, 7.0 Hz); 7.61 (1H, d, 7.0 Hz); 7.83 (1H, m); 10.60 (1H, bs); 10.95 (1H, bs).

IR (KBr): 740, 800, 960, 1120, 1130, 1340, 1490, 1610, 2600, 2925 and 3250 cm⁻¹.

EXAMPLE 16

1-[2-(1H-indol-3-yl)-ethyl]-4[6-methoxy-2-pyridinyl-piperazine hydrate

A mixture of 3-(2-bromoethyl)indole (1.66 g), 1-(6-methoxy-2-pyridinyl)piperazine (2.86 g), micropulverized K₂CO₃ (2.04 g) and tetrabutylammonium hydrogen sulfate 0.13 g) in acetonitrile (50 mL) was heated at reflux under N₂ atmosphere for 2 h. The excess acetonitrile was removed under reduced pressure and water (10 mL) added to the concentrate. The aqueous phase was extracted with CH₂Cl₂ (3×50 mL). The combined CH₂Cl₂ extracts were washed with sat. NaCl solution, dried with anhydrous K₂CO₃, and concentrated under reduced pressure. Silica gel chromatography. (CH₂Cl₂/MeOH; 96:4) of the residue yielded the free base of the desired Ia product (2.20 g; 89%).

Anal. Calcd. for $C_{20}H_{24}N_O.0.5\ C_2H_6O.0.5\ H_2O$:

C, 68.46; H, 7.66; N, 15.21; H₂O, 2.45

Found: C, 68.24; H, 7.59; N, 15.35; H₂O, 2.30.

NMR (CDCl₃) 2.70 (6H, m); 3.08 (2H, m); 3.61 (4H m); 3.90 (3H, s); 6.11 (1H, d, 9.5 Hz); 6.20 (1H, d, 9.0 Hz); 7.12 (3H, m); 7.40 (2H, m); 7.68 (1H, m); 8.00 (1H, bs).

IR (KBr): 745, 790, 985, 1250, 1450, 1460, 1590, 2840, 3180 and 3550 cm⁻¹.

EXAMPLE 17

1-[2-(1H-indol-3-yl)-ethyl]-4-[3-trifluoromethyl-2-pyridinyl]piperazine hydrochloride A mixture of 3-(2-bromoethyl)indole (1.79 g), 1-(3-trifluoromethyl-2-pyridinyl)piperazine (1.85 g), micropulverized K₂CO₃ (2.21 g) and tetrabutylammonium hydrogen sufate (0.014 g) in acetonitrile (50 mL) was heated at reflux under N₂ atmosphere for 3 h. The excess acetonitrile was removed under reduced pressure and water (10 mL) added tothe concentrate. The aqueous phase was extracted with CH₂Cl₂ (3×50 mL). The combined CH₂Cl₂ extracts were washed with sat. NaCl solution, dried with anhydrous K₂CO₃, and concentrated urnder reduced pressure. Silica gel chromatography (CH₂Cl₂/MeOH; 97.3) of the residue yielded the free base (1.66 g; 56%) which was treated with ethanolic HCl to yield the hydrochloride salt of the desired Ia product (1.45 g; 80%).

Anal Calcd for $C_{20}H_{21}N_4F_3.HCl$:

C, 58.47; H, 5.40; N, 13.64

Found: C, 58.60; H, 5.43; N, 13.66.

NMR (DMSO-d ): 3.30 (10H, m); 3.72 (2H, m); 7.08 (2H, m); 7.22 (1H, d, 4.9 Hz); 7.35 (2H, m); 7.66 (1H, m); 8.12 (1H, m); 8.60 (1H, m).

IR (KBr): 750, 1040, 1130, 1320, 1450, 1580, 1595 2460, 2580 and 3230 cm⁻¹.

EXAMPLE 18

1-[2-(1H-indol-3-yl)-ethyl]-4-[3-methoxy-2-pyridinyl]-piperazine

A mixture of 3-(2-bromoethyl)indole (2.00 g), 1-(3-methoxy-2-pyridinyl)piperazine (1.72 g), micropulverized K₂CO₃ (2.46 g) and tetrabutylammonium hydrogen sulfate (0.15 g), in acetonitrile (50 mL) was heated at reflux under N₂ atmosphere for 5 h. The excess acetonitrile was removed under reduced pressure and water (10 mL) was added to the concentrate. The aqueous phase was extracted with CH₂Cl₂ (3×50 mL). The combined CH₂Cl₂ extracts were washed with sat. NaCl solution, dried with anhydrous K₂CO₃, and concentrated under reduced pressure. Silica gel chromatography (CH₂Cl₂/MeOH; 96.4) of the residue yielded the free base of the desired Ia product (1.32 g; 44%).

Anal. Calcd. for $C_{20}H_{24}N_4O$:

C, 71.41; H, 7.20; N, 16.66

Found: C, 71.34; H, 7.23; N, 16.55.

NMR (CDCl₃): 2.80 (6H, m); 3.04 (2H, m); 3.55 (4H, m); 3.90 (3H, s); 6.86 (1H, dd, 4.8, 7.6 Hz); 7.14 (4H, m); 7.36 (1H, m); 7.66 (1H, m); 7.92 (1H, dd, 1.4, 4.8 Hz); 8.14 (1H, bs).

IR (film): 740, 1210, 1240, 1440, 1450, 1470, 1590, 2840, 2940, 3200 and 3450 cm⁻¹.

EXAMPLE 19

1-(6-Chloro-2-pyridinyl)-4-[3-(1H-indol-3-yl)propyl]-piperazine hydrochloride An acetonitrile solution (25 mL) containing 3-(3-bromopropyl)indole (V; 1.51 g), 1-(6-chloro-2-pyridinyl)piperazine (III; 2.50 g), micropulverized $K_2CO_3$ (1.75 g), and tetrabutylammonium hydrogen sulfate was heated at reflux with stirring and under $N_2$ atmosphere for 1 h. Excess acetonitrile was removed under reduced pressure and the remaining mixture was extracted with $CH_2Cl_2$. The solid residue was dissolved in water (10 mL) and extracted with $CH_2Cl_2$. The combined organic extracts were dried with anhydrous $K_2CO_3$, filtered and concentrated under reduced pressure to afford a viscous material. Silica gel chromatography (EtOAc/$CH_2Cl_2$; 4:1) yielded the free base (1.67 g; 74%) which was treated with ethanolic HCl to provide the hydrochloride salt of the desired Ia product (1.6 g; 87%).

Anal. Calcd. for $C_{20}H_{23}ClN_4 \cdot HCl$:
C, 61.39; H, 6.19; N, 14.32
Found: C, 61.49, H, 6.24; N, 14.35.

NMR (DMSO-$d_6$): 2.14 (2H, m); 2.80 (2H, t, 6.9 Hz); 3.18 (4H, m); 3.55 (4H, m); 4.36 (2H, d, 13.6 Hz); 6.82 (1H, d, 8.1 Hz); 6.91 (1H, d, 8.1 Hz); 7.05 (3H, m); 7.40 (1H, d, 92 Hz); 7.62 (2H, m); 11.00 (1H, bs); 11.55 (1H, bs).

IR (KBr): 740, 785, 950, 1130, 1260, 1440, 1590, 2600, 2920 and 3150 cm$^{-1}$.

EXAMPLE 20

1-[3-(1H-indol-3-yl)-propyl]-4-[3-methoxy-2-pyridinyl]-piperazine dihydrochloride hydrate A mixture of 3-(3-bromopropyl)indole (1.55 g), 1-(3-methoxy-2-pyridinyl)piperazine (2.51 g), micrppulverized $K_2CO_3$ (1.79 g) and tetrabutylammonium hydrogen sulfate (b 0.11 g) in acetonitrile (100 mL) was heated at reflux under $N_2$ atmosphere for 3 h. The excess acetonitrile was remoVed under reduced pressure and water (15 mL) added to the concentrate. The aqueous phase was extracted with $CH_2Cl_2$ 3×60 mL). The combined $CH_2Cl_2$ extracts were washed with sat. NaCl solution, dried with anhydrous $K_2CO_3$, filtered and concentrated under reduced pressure. Silica gel chromatography ($CH_2Cl_2$/MeOH; 95:5) of the residue yielded the free base which was treated with ethanolic HCl to yield the dihydrochloride salt of the desired Ia product (1.30 g; 45%)

Anal. Calcd for $C_{21}H_{26}N_4O \cdot 2HCL \cdot 0.95\ H_2O$:
C, 57.27; H, 6.85; N, 12.72; $H_2O$, 3.89
Found: C, 57.67; H, 6.82; N, 12.67; $H_2O$, 4.18.

NMR (DMSO-$d_6$) 2.16 (2H, m); 2.78 (2H, t, 6.7 Hz); 3.20 (6H, m) 3.57 (2H, d, 12.5 Hz); 3.85 (3H, S); 4.08 (2H, d, 12.5 Hz); 4.80 (3H, bs); 7.02 (4H, m); 7.39 (2H, m); 7.56 (1H d, 7.8 Hz); 7.81 (1H, dd, 5.8, 0.8 Hz); 10.85 (2H, bs).

IR (KBr): 760, 770, 1010, 1255, 1430, 1470, 1555, 1610, 2450, 2910 and 3210 cm$^{-1}$.

By Process 2. (Ia Products)

EXAMPLE 21

1-[4-(1H-indol-3-yl)butyl]-4-(3-methoxy-2-pyridine-1)piperazine dihydrochloride Borane-methyl sulfide complex (3.3 mL; 2.0 M THF soln.) was added dropwise to a THF (9 mL) solution containing 1-[4-(indol-3-yl)-1-oxobutyl]-4-(3-methoxy-2-pyridinyl)piperazine (IV; 1.0 g) at 0° C. while under N atmosphere. After the addition was complete, the reaction was heated at reflux for 3 h. Upon cooling to 0° C., MeOH (5 mL) was added and the reaction allowed to stand 20 h at 22° C. The reaction was cooled to 0° C. and HCl gas introduced until a pH<2 was attained, after which the solution was gently refluxed for 1 h. The reaction was cooled, MeOH (10 mL) added, and concentrated under reduced pressure. The residue was heated atreflux in 4 N acetic acid for 5 h. After cooling, the reaction was made basic with 10 N NaOH (pH>10) and extracted with $Et_2O$. The combined $Et_2O$ extracts were dried with anhydrous $K_2CO_3$, filtered, and concentrated under reduced pressure. Silica gel chromatography (EtOAc/MeOH; 97:3) aforded the free base which was treated with ethanolic HCl to provide the dihydrochloride of the desired Ia product (83 mg; 8%).

Anal. Calcd. for $C_{22}H_{28}N_4O \cdot 2HCl$:
C, 60.42; H, 6.92; N, 12.81
Found: C, 60.15; H, 6.73; N, 12.67.

NMR (DMSO-$d_6$) 1.73 (4H, m); 2.74 (2H, t, 6.6 Hz); 318 (4H, m); 3.33 (2H, m); 3.53 (2H, d, 12.0 Hz); 4.00 (v, m, bs, $CH_2$, H$^+$, $H_2O$); 3.85 (3H, s); 7.04 (3H, m); 7.16 (1H, d, 2.2 Hz); 7.34 (1H, d, 7.6 Hz); 7.42 (1H, dd, 8.0, 1.2 Hz); 7.52 (1H, d, 7.2 Hz); 7.83 (1H, dd, 5.2, 1.2 Hz).

IR (KBr): 740, 805, 1000, 1270, 1460, 1550, 1560, 1600, 2570, 2930 and 3250 cm$^{-1}$.

EXAMPLE 22

4-[6-Chloro-2-pyridinyl]-1-[2-(1H-indol-3-yl)-propyl]-piperazine

To a mixture of 1-(6-chloro-2-pyridyl)piperazine (1.418 g, 7.2 mmol), triethylamine hydrochloride (994 mg, 7.2 mmol) and $NaCNBH_3$ (1.512 g, 24 mmol) in 12 mL of dry tetrahydrofuran was added a solution of 3-(2-oxopropyl)indole (416 mg, 2.4 mmol) in 5 mL of tetrahydrofuran. The reaction mixture was vigorously stirred at room temperature under Ar for 17 h and then it was poured into saturated aqueous $NaHCO_3$ and extracted with ethyl acetate (×3). The organic phase was washed with $H_2O$, (×2) and 0.1N HCl (25 mL) and then it was dried ($Na_2SO_4$) and evaporated to give a gum. Chromatography ($SiO_2$/$CH_2Cl_2$-acetonitrile=1:1) of this gum gave the product (714 mg, 84%) as a white foam.

$^1$NMR ($CDCl_3$)
δ7.98 (br s, 1H), 7.64–7.59 (m, 1H), 7.43–7.343 (m, 2H), 7.24–7.08 (m, 2H), 7.06 (d, J=2.3 Hz, 1H), 6.59 (d, J=7.3 Hz, 1H), 6.50 (d, J=8.4 Hz, 1H), 3.62–3.57 (m, 4H), 3.18—3.09 (m, 1H) 3.06–2.93 (m, 1H) 2 79–2.74 (m 4H) 2.65 (dd, J=13.5, 9.1 Hz, 1.03 (d, J=6.5 Hz, 3H).

The hydrochloride was prepared by treating an ethereal solution of the product with anhydrous HCl. The resulting white fluffy solid was crystallized from ethanol-ether to give the hydrochloride salt (660 mg, 85%) as a white, microcrystalline solid: m.p. 242°-244° C. (dec).

By Process 3 (Ib and Ic Products)

EXAMPLE 23

3-[4-[4-(6-Chloro-2-pvridinyl)-1-piperazinyl]-1cyclohexen-1-yl]-5-methoxy-1H-indole A solution of 5-methoxyindole (0.26 g, 1 8 mmole), 4-[4-(6-chloro-2-pyridinyl)-1-1-piperazinyl]-cyclohexane-1one (VIII; 0.50 g, 1.7 mmole), and pyrrolidine (0 5 mL) in ethanol (10 mL) was refluxed for 18 h. The solution was concentrated in vacuo and the residue chromatographed on silica gel using ethyl acetate as the eluent to give the desired product of formula Ib (0.59 g, 82%., m.p. 210°-213° C.).

Anal Calcd. for $C_{27}H_{27}ClN_4O$:
C, 68.16; H, 6.44; N, 13.25
Found: C, 68.00; H, 6.57; N, 12.97
NMR(DMSO-$d_6$): 1.52 (1H, m); 2.04 (1H, m), 2.22 (1H, m); 2.0 (2H, m); 2.64 (6H, m); 3.48 (4H, m); 3.75 (3H, s); 8.07 (1H, m); 6.63 (1H, d, 7.4 Hz); 6.75 (2H, m); 7.26 (3H, m); 7.53 (1H, dd, 7.9, 8.1 Hz); 10.91 (1H, bs).
IR (KBr): 780,800, 980, 1140, 1260, 1450, 1480, 1550, 1600, 2840 and 2920 cm$^{-1}$.

EXAMPLE 24

3-[4-[4-(Substituted-2-pyridinyl)-1-piperazinyl]-1-cyclohexan-1-yl]-1H-indole 4-(1H-indol-3-yl)cyclohex-3-enone, ethylene ketal, XII Indole (1.17 g, 10 mmol), 1.4-cyclohexanedione monoethylene ketal (1.95 g, 12.5 mmol), and pyrrolidine (1.77 g, 25mmol, 2.1 mL) were refluxed in ethanol (50 mL) for 3 days The solution was concentrated in vacuo. The residue was washed with ethyl acetate (30 mL) and the solid product was collected and dried (yield: 2.05 g, 80%). The product was recrystallized from methanol (20 mL) to give compound XII as a white powder (1.75 g).

4-(1H-indol-3-yl)cyclohexanone, XI

Compound XII (1.75 g, 6.9 mmol) was hydrogenated for 18 h at 60 psi using 10% Pd/C (0.15 g). The mixture was filtered and the filtrate concentrated in vacuo. The residue was refluxed for 18 h in acetone (150 mL) with water (10 mL) and p-toluene sulfonic acid (0.10 g). Sodium carbonate (5.0 g) was added and the mixture refluxed for 30 min. The mixture was cooled and filtered, and the filtrate was concentrated in vacuo. The residue was chromatographed on silica gel using ethyl acetate as the eluent to give the XI desired product (129 g, 88%).

3-[4-(4-(Substituted-2-pyridinyl)-1-piperazinyl)-1-cyclohexyl]-1H-indole, Ic

A mixture of compound II (10 mmol), the desired substituted-pyridinyl piperazine (III; 10 mmol), and titanium(IV) isoprcpoxide (3.72 mL, 12.5 mmol) would be stirred until the IR spectrum of the mixture showed no remaining ketone band (gentle heating may be required). The viscous solution would then be diluted with ethanol (10–20 mL) and sodium cyanoborohydride (0.42 g, 6.7 mmol) added. After stirring for 20 hr, water (2 mL) would be added and the resulting inorganic precipitate filtered and washed with ethanol. The filtrate could then be concentrated in vacuo and the crude product purified by chromatography on silica gel. Alternately, cyclchexenyl products of Formula Ib may be hydrogenated to yield products of Formula Ic in cases where other substituents on the precursor molecule are stable to the hydrogenation process Compound preparation data for these and other Formula I compounds, prepared in a manner similar to the above procedures, is shown in Table 1. Selection of appropriate starting materials and intermediates as well as adjustments of the procedures would be well within the skill of one skilled in the art.

TABLE 1

| Ex. No. | Structure | % Yield | MP (°C.) | Cryst. Sol. |
|---|---|---|---|---|
| 14 | (indole-ethyl-piperazine-pyridinyl-Cl) .HCl | 77 | 250-252 | EtOH |
| 15 | (indole-ethyl-piperazine-pyridinyl-$CF_3$) .HCl | 68 | 206-208 | EtOH |
| 16 | (indole-ethyl-piperazine-pyridinyl-OMe) .solvate | 89 | 60-85 | EtOH |

TABLE 1-continued
Formula I Compounds
| Ex. No. | Structure | % Yield | MP (°C.) | Cryst. Sol. |
|---|---|---|---|---|
| 17 | 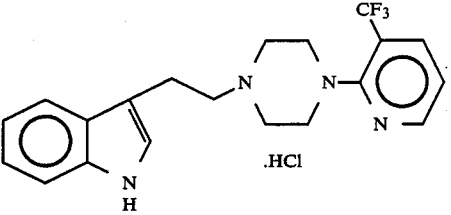 .HCl | 80 | 242–243 | EtOH |
| 18 | 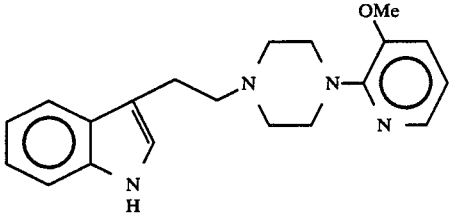 | 44 | 138–140 | EtOH |
| 19 | 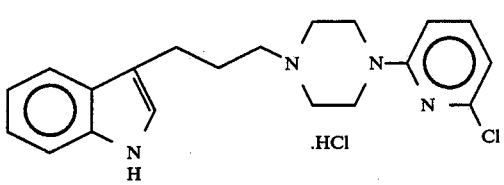 .HCl | 87 | 221–222 | EtOH |
| 20 | 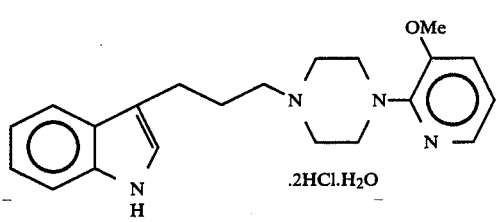 .2HCl.H₂O | 45 | 216–219 | EtOH |
| 21 | 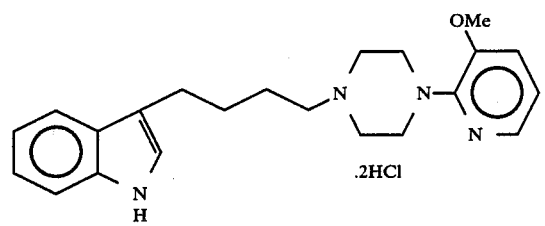 .2HCl | 23 | 228–230 | EtOH |
| 22 | 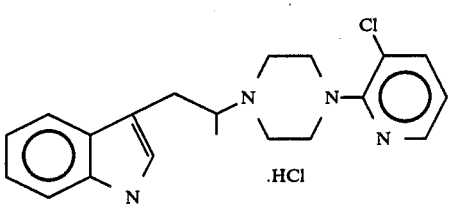 .HCl | | | |
| 23 | 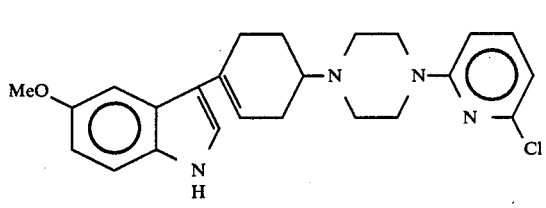 | 82 | 210–213 | EtOAc |

TABLE 1-continued

| Ex. No. | Structure | % Yield | MP (°C.) | Cryst. Sol. |
|---|---|---|---|---|
| 25 | (indole-CH₂CH₂-piperazine(Me)-pyridine(OMe)) .2HCl | 11 | 155–194 | EtOH |
| 26 | (indole-CH₂CH₂-bicyclic N-pyridine(OMe)) (1r,4r) .hydrate | 4 | 55–60 | EtOH |
| 27 | (indole-CH₂CH₂-bicyclic N-pyridine(OMe)) .2HCl (1s,4s) | 43 | 234–236 | iPrOH/EtOH/THF |
| 28 | (indole-CH₂CH₂-bicyclic N-pyridine-Cl) .HCl (1s,4s) | 67 | 239–241 | iPrOH/EtOH |
| 29 | (indole-CH₂CH₂-bicyclic N-pyridine-Cl) .HCl (1r,4r) | 53 | 239–242 | iPrOH/EtOH |
| 30 | (indole-(CH₂)₃-piperazine-pyridine-CF₃) .HCl | 14 | 212–214 | Hex/CH₂Cl₂ |
| 31 | (indole-(CH₂)₄-piperazine-pyridine-Cl) .hydrate | ~1 | 99–101 | EtOH |

TABLE 1-continued

Formula I Compounds

| Ex. No. | Structure | % Yield | MP (°C.) | Cryst. Sol. |
|---|---|---|---|---|
| 32 | [indole-(CH₂)₄-piperazine-pyridine-6-CF₃] | 50 | 83–86 | Hex/CH₂Cl₂ |
| 33 | [indole-(CH₂)₃-piperazine-pyridine-4-CF₃] | 28 | 90–93 | EtOH |
| 34 | [indole-(CH₂)₃-bicyclic diamine-pyridine-3-OMe] .oxalate (1s,4s) | 22 | 103–125 | MeOH |
| 35 | [indole-(CH₂)₃-bicyclic diamine-pyridine-3-OMe] .2HCl (1r,4r) | 64 | 155–186 | EtOH |
| 36 | [indole-CH₂-CH(CH₃)-piperazine-pyridine-6-Cl] .HCl | 85 | 242–244 | Et₂O/CH₃CN/EtOH |
| 37 | [indole-(CH₂)₂-piperazine-pyridine-4-CF₃] .HCl | 21 | 150–225 | EtOH |
| 38 | [5-MeO-indole-(CH₂)₂-piperazine-pyridine-3-OMe] .2HCl | 35 | 182–185 | MeOH/EtOAc |

TABLE 1-continued

Formula I Compounds

| Ex. No. | Structure | % Yield | MP (°C.) | Cryst. Sol. |
|---|---|---|---|---|
| 39 | 5-F-indole-CH₂CH₂-piperazine-(3-OMe-pyridin-2-yl) | 36 | 140–142 | EtOAc |
| 40 | 5-MeO-indole-CH₂CH₂-piperazine-(6-Cl-pyridin-2-yl) · HCl | 19 | 195–196 | MeOH/Et₂O |
| 41 | 5-F-indole-CH₂CH₂-piperazine-(6-Cl-pyridin-2-yl) · HCl | 23 | 205–208 | MeOH/EtOAc |
| 42 | indole-CH₂CH₂-piperazine-(3-Cl-pyridin-2-yl) · HCl | 42 | 213–216 | EtOH |
| 43 | 5-F-indole-CH₂CH₂-piperazine-(6-CF₃-pyridin-2-yl) | 43 | 115–116 | Ethyl acetate/hexane |
| 44 | 5-MeO-indole-CH₂CH₂-piperazine-(6-CF₃-pyridin-2-yl) | 31 | 140–142 | Ethyl acetate/hexane |
| 45 | tetrahydrocarbazole-piperazine-(6-Cl-pyridin-2-yl) · fumarate | 66 | 226–230 | MeOH |

TABLE 1-continued

Formula I Compounds

| Ex. No. | Structure | % Yield | MP (°C.) | Cryst. Sol. |
|---|---|---|---|---|
| 46 | 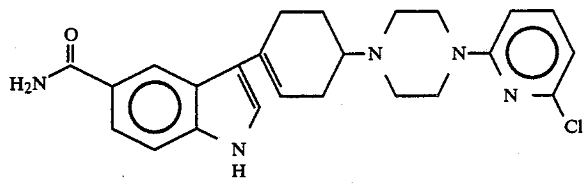 | 63 | 225-230 | 10% MeOH/EtOAc |
| 47 | 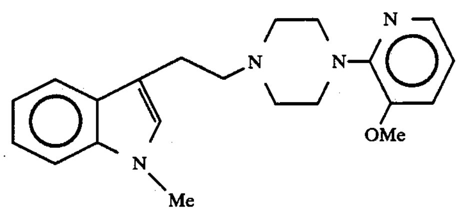 | 46 | 125-127 | Ethyl acetate |
| 48 | 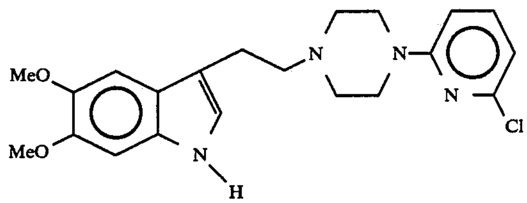 | 45 | 137-139 | Ethyl acetate |
| 49 | 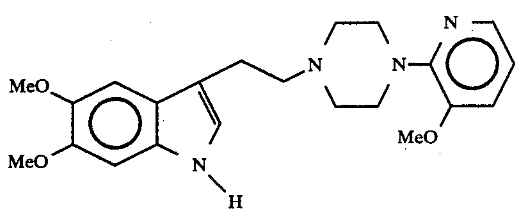 | 42 | 160-163 | Ethyl acetate |
| 50 | 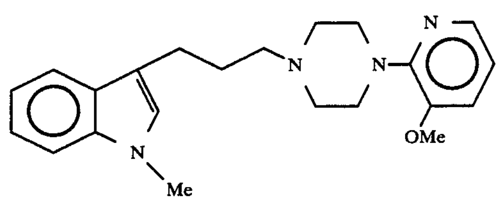 | 92 | 187-189 | EtOH |
| 51 | 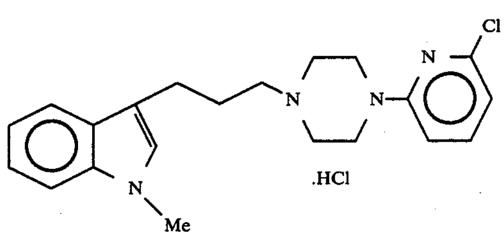 | 83 | 200-203 | EtOH |
| 52 | 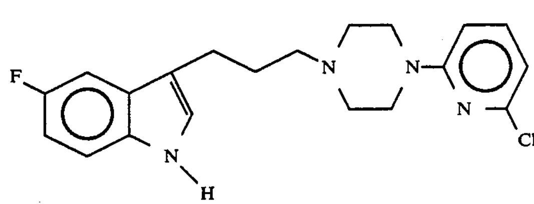 | 81 | 210-212 | EtOH |

TABLE 1-continued

| Ex. No. | Structure | % Yield | MP (°C.) | Cryst. Sol. |
|---|---|---|---|---|
| 53 | 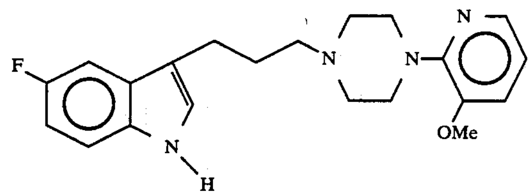 | 72 | 127 | CH$_2$Cl$_2$/Et$_2$O/hexane |
| 54 | 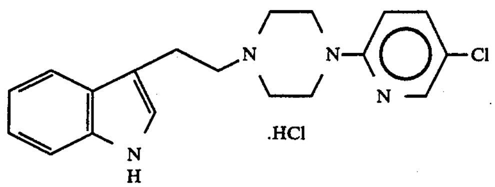 | 38 | 253–255 | EtOH |
| 55 | 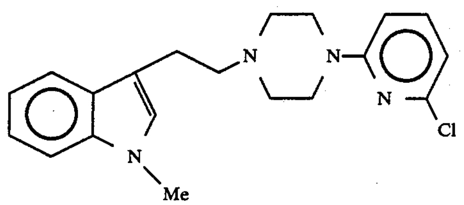 | 72 | 115–116 | Ethyl acetate |
| 56 | 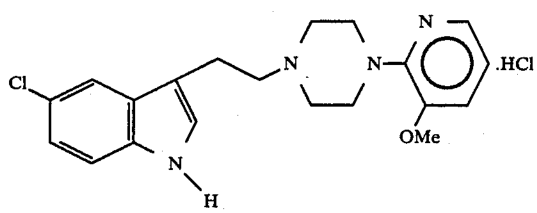 | 41 | 205–207 | Ethyl acetate |
| 57 | 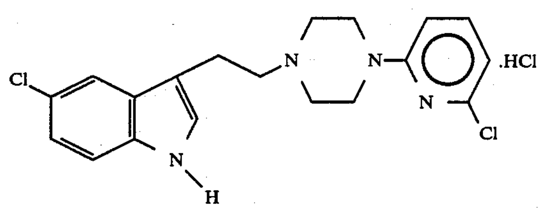 | 40 | 238–242 | MeOH/Et$_2$O |

TABLE 2

Biological Activities of Formula I Compounds: Inhibition of Serotonin Uptake (in vitro)

| Ex. No. | IC$_{50}$ (nM) | Ex. No. | IC$_{50}$ (nM) |
|---|---|---|---|
| 14 | 74 | 36 | 75 |
| 15 | 73 | 37 | 386 |
| 16 | 88 | 38 | 11 |
| 17 | 37 | 39 | 0.2 |
| 18 | 13 | 40 | 177 |
| 19 | 98 | 41 | 2.8 |
| 20 | 1.1 | 42 | 520 |
| 21 | 58 | 43 | 73 |
| 23 | 99 | 44 | 560 |
| 25 | 8.6 | 45 | 100 |
| 26 | 106 | 46 | 27 |
| 27 | 12.5 | 47 | 24 |
| 28 | 77 | 48 | 127 |
| 29 | 106 | 50 | 3.7 |
| 30 | 192 | 51 | 86 |
| 31 | 27 | 54 | 30 |
| 32 | 259 | 55 | 126 |
| 33 | 105 | | |
| 34 | 5.6 | | |
| 35 | 152 | | |

Additional Detailed Description of the Invention

Some additional compounds of Formula I have been made, tested and found to have useful CNS properties particularly antidepressant properties. The additional compounds were prepared by employing the synthetic processes described hereinabove, using alterations which would be apparent to a skilled chemist in order to produce the desired product compound Some additional examples are given here for further guidance.

Additional Intermediate Compounds.

Compounds of Formula III

EXAMPLE 58

1-6-Chloro-2-pyridinyl)-2-methylpiperazine

A mixture of 2-methylpiperazine (21.31 g), 2,6-dichloropyridine (10.0 g) and micropulverized $K_2CO_3$ (27.99 g) in $CH_3CN$ (200 mL) was heated at reflux under nitrogen atmosphere for 24 h. The reaction was filtered and the filtrate concentrated under reduced pressure. The concentrate was dissolved in $CH_2Cl_2$ and extracted with 5% $NaHCO_3$ and water. The organic phase was dried with $K_2CO_3$, filtered and concentrated under reduced pressure. Silica gel chromatography ($CH_2Cl_2$/MeOH/$NH_4OH$; 96:4:0:4) of the residue yielded product: (13.34 g, 93%).

EXAMPLE 59

1-(3-Methoxy-2-pyridinyl)-2-methylpiperazine

A mixture of 2-methylpiperazine (6.66 g) and 2-bromo-3-methoxypyridine (2.5 g) was heated in an autoclave at 100° C. for 24 h. The reaction mixture was dissolved in $CH_2Cl_2$ and extracted with 5% $NaHCO_3$ and water. The organic phase was dried with $K_2CO_3$, filtered, and concentrated under reduced pressure. Silica gel chromatography ($CH_2Cl_2$/MeOH/$NH_4OH$; 92:8:8.0) of the residue yielded the product (2.28 g, 83%).

EXAMPLE 60

1-(5-Chloro-3-methoxy-2-pyridinyl)piperazine (a) 2-bromo-5-chloro-3-pyridinol A solution of bromine (12.35 g) in 10% NaOH (70 mL) was added dropwise with stirring to a solution of 5-chloro-3-pyridinol (10.00 g) in 10% NaOH (70 mL). After the addition was complete, the reaction was stirred at 22° C. for 20 h. The reaction was cooled to 0° C. and acidified to pH 5.3 with concentrated HCl (aq). The precipitate was filtered and dried under vacuum for 60 h to afford a) (15.66 g, 97%).

(b) 2-bromo-5-chloro-3-methoxypyridine

To a stirred mixture of 2-bromo-5-chloro-3-pyridinol (15.66 g) and pulverized KOH (16.79 g) in DMSO (100 mL) at 55–60° C. was added dropwise a solution of $CH_3I$ (13.27 g) in DMSO (35 mL) while under nitrogen atmosphere. After the addition was complete, the reaction was maintained at 55°–60° C. for 1 h. The reaction was extracted with $Et_2O$ (3×150 mL) and the combined $Et_2O$ extracts were treated in turn with 1N NaOH (150 mL), water (150 mL), 1N HCl (150 mL), water (150 mL), and a saturated NaCl solution (150 mL). The organic phase was dried with $MgSO_4$, filtered, and concentrated under reduced pressure to yield a solid material. Recrystallization of the solid from hexane afforded b) (3.52 g, 21%).

(c) 1-(5-chloro-3-methoxy-2-pyridinyl)piperazine

Anhydrous piperazine (13.41 g) and 2-bromo-5-chloro-3-methoxypridine (3.50 g) were heated in an autoclave at 100° C. for 20 h. The mixture was dissolved in water (10 mL) and extracted with $CH_2Cl_2$ (3×100 mL). The combined organic extracts were washed with a saturated NaCl soution, dried with $K_2CO_3$, filtered and concentrated under reduced pressure. Silica gel chromatography ($CH_2Cl_2$/MeOH; 90:10) of the residue yielded product (1.17 g, 33%).

Compounds of Formula V

EXAMPLE 61

3-2-Bromoethyl)-1-methylindole (a) Methyl 1-methylindole-3-acetate

A dispersion of 35% KH in oil (21.0 g, 0.18 mol) was washed free of oil with dry pentane under an Ar atmosphere To a suspension of the resulting solid in 100 mL of dry dimethylformamide was added a solution of indole-3-acetic acid (10.5 g, 0.060 mol) in 60 mL of dimethylformamide, dropwise at −20° C. under Ar. The mixture was stirred at the same temperature for 2 h and then $CH_3I$ (12.0 ml, 0.19 mol) was added dropwise. Stirring was continued at −20° to 10° C. for 2½ h and then the mixture was stored at 5° C. for 16 h. Ether was then added and the mixture was washed ($H_2O$, brine), dried ($Na_2SO_4$) and evaporated to give an orange oil. Flash chromatography ($SiO_2$/10–20% ethyl acetate-hexane×2) of this oil afforded the product (5.25 g, 43%) as an oil: IR (near) 1745 cm$^{-1}$; $^1$Hnmr (80 MHz, $CDCl_3$) δ 7.75–7.55 (m, 1H), 7.40–7.07 (m, 4H), 3.83 (s, 2H), 3.80 (s, 3H), 3.75 (s, 3H).

(b) 3-(2-Hydroxyethyl)-1-methylindole

To a suspension of $LiAlH_4$ (2.0 g, 0.052 mol) in 50 mL of dry tetrahydrofuran was added dropwise a solution of methyl 1-methylindole-3-acetate (5.25 g, 0.026 mol) in 70 mL of dry tetrahyqrofuran at −10° C. under Ar. The mixture was refluxed for 1 h and then it was cooled at 0° C. and quenched by the sequential addition of 2 mL of $H_2O$, 2 mL of 15% aqueous NaOH and finally 6 mL of $H_2O$. The resulting slurry was filtered and the filter cake was washed with additional tetrahydrofuran. Evaporation of the filtrate gave the product (40 g, 89%) as an oil which was used without further purification.

(c) 3-(2-Bromoethyl)-1-methylindole

To a solution of 1-methyl-3-(2-hydroxyethyl)indole (4.00 g, 0.023 mol) in 50 mL of acetonitrile at −20° C. under Ar was added a solution of $CBr_4$ (10.16 g, 0.031 mol) in 25 mL of acetonitrile, followed by a solution of triphenylphosphine (8.00 g, 0.031 mol) in 125 mL of acetonitrile. The mixture was stirred and allowed to warm to 0° C. over 2 h. The resulting mixture was evaporated and the residue was chromatographed ($SiO_2$/hexane, then ethyl acetate-hexane=1:4) to give the product (4.00 g, 74%) as a brown oil: IR (neat) 2940, 1617, 1552 cm$^{-1}$; $^1$Hnmr (200 MHz, $CDCl_3$) δ 7.58 (d, J=7.6 Hz, 1H), 7.33–7.09 (m, 3H), 6.95 (s, 1H), 3.77 (s, 3H), 3.62 (t, J=7.9 Hz, 2H), 3.32 (t, J=7.7 Hz, 2H).

EXAMPLE 62

3-[1-Methyl-3-(p-toluenesulfonyloxy)propyl]indole

To a suspension of $LiAlH_4$ (1.50 g, 39 mmol) in 100 mL of dry THF at −10° C. under Ar was added a solution of ethyl 3-(3-indolyl)-3-methylpropionate[1] (7.00 g, 30 mmol) in 50 mL of THF. The mixture was stirred at room temperature for 3 h and then it was quenched at 0° C. with 2 mL of $H_2O$. The resulting slurry was filtered and the filter cake was washed with THF. The filtrate was then dried ($Na_2SO_4$) and evaporated to give the intermediate VI product, 3-(1-methyl-3-hydroxypropyl)indole (5.05 g, 88%) as an oil: IR (neat) 3420, 3300 cm$^{-1}$.

To an ice cold solution of 3-(1-methyl-3-hydroxypropyl)indole (5.00 g. 0.026 mol) in 100 mL of $CH_2C_{;2}$ was added triethylamine (4.1 mL, 0.03 mol), p-toluenesulfonyl chloride (5.50 g, 0.029 mol) and 4-N,N-dimethylaminopyridine (DMAP) (0.6 g). The mixture was stirred at room temperature under Ar for 18 h and then it was evaporated and the residue was chromatographed (SiO$_2$/ethyl acetate-hexane=1:0, then ethyl acetate) to give the product (7.75 g, 86%) as a light brown gum: IR (neat) 3420, 1357, 1175 cm$^{-1}$.
1. Oikawa, et. al., *Tetrahedron Lett.,* 1759 (1978).
Additional Formula I Compounds.

EXAMPLE 36 - ALTERNATE PREPARATION
3-[2-[4-(6-Chloro-2-pyridyl)-1-piperazinyl]propyl]-indole To a mixture of 1-(6-chloro-2-pyridyl)piperazine (1.418 g. 7.2 mmol), triethylamine hydrochloride (994 mg, 7.2 mmol) and NaCNCH$_3$ (1.512 g, 24 mmol) in 12 mL of dry tetrahydrofuran was added a solution of 3-(2-oxopropyl)indole (416 mg, 2.4 mmol) in 5 mL of tetrahydrofuran. The reaction mixture was vigorously stirred at room temperature under Ar for 17 h and then it was poured into saturated aqueous NaHCO$_3$ and extracted with ethyl acetate (×3). The organic phase was washed with H$_2$O (×2) and 0.1N HCl (25 mL) and then it was dried (Na$_2$SO$_4$) and evaporated to give a gum. Chromatography (SiO$_2$/CH$_2$Cl$_2$-acetonitrile=1:1) of this gum gave the product (714 mg, 84%) as a white foam: $^1$Hnmr (200 MHz, CDCl$_3$) δ 7.98 (br, s, 1H), 7.64–7.5(m, 1H), 7.43–7.343 (m, 2H), 7.24–7.08 (m, 2H), 7.06 (d, J=2.3 Hz, 1H), 6.59 (d, J=7.3 Hz, 1H), 6.50 (d, J=8.4 Hz, 1H, 3.62–3.57 (m, 4H), 3.18–3.09 (m, 1H), 3.06–2.93 (m, 1H), 2.79–2.74 (m, 4H), 2.65 (dd, J=13.5, 9.1 Hz, 1H), 1.03 (d, J=6.5 Hz, 3H). The hydrochloride salt was prepared by treating an ethereal solution of the product with anhydrous HCl. The resulting white fluffy solid was crystallized from ethanol-ether to give the hydrochloride salt (660 mg, 85%) as a white, microcrystalline solid: m.p. 242°–244° C. (dec); IR KBr) 3430, 3190, 1590 cm$^{-1}$.

Additional Formula I compounds which have been prepared by appropriate modifications of the reaction schemes and procedures given hereinabove, are displayed in Table IA.

TABLE 1A

Additional Formula I Compounds

| Ex. No. | Structure | % Yield | MP (°C.) | Cryst. Sol. |
|---|---|---|---|---|
| 63 | 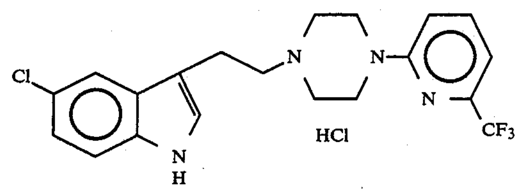 | 49 | 158–62 | Me$_2$CO—Et$_2$O |
| 64 | 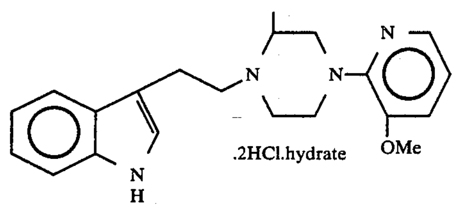 | 53 | 174–85 | EtOH—ET$_2$O |
| 65 | 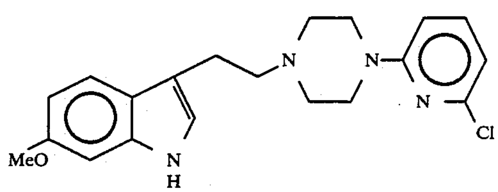 | 69 | 103–05 | EtOAc |
| 66 | 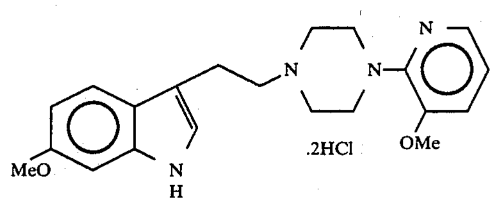 | 41 | 218 | MeOH—Et$_2$O |
| 67 | 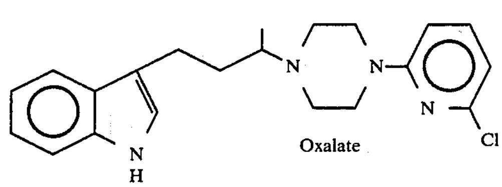 | 44 | 110–115 | MeOH—THF |

TABLE 1A-continued
Additional Formula I Compounds

| Ex. No. | Structure | % Yield | MP (°C.) | Cryst. Sol. |
|---|---|---|---|---|
| 68 | (indole-CH₂CH(CH₃)-N-piperazine-N-(3-methoxypyridin-2-yl)) Oxalate | 30 | 55 | Et₂O |
| 69 | (5,6-dimethoxyindole-CH₂CH₂-N-piperazine-N-(6-trifluoromethylpyridin-2-yl)) | 43 | 122–25 | EtOAc |
| 70 | (5-fluoroindole-cyclohexenyl-N-piperazine-N-(3-chloropyridin-2-yl)) .hydrate | 15 | 168–170 | EtOAc |
| 71 | (indole-(CH₂)₃-N-piperazine-N-(3-methoxy-6-chloropyridin-2-yl)) .HCl.hydrate | 65 | 194–98 | EtOH |
| 72 | (indole-(CH₂)₃-N-(methylpiperazine)-N-(6-chloropyridin-2-yl)) | 65 | 132–35 | EtOH |

TABLE 2A
Biological Activities of Some Additional Formula I Compounds Inhibition of Serotonin Uptake (in vitro)

| Ex. No. | IC₅₀ (nM) | Ex. No. | IC₅₀ (nM) |
|---|---|---|---|
| 56 | <1 | 67 | 142 |
| 57 | 166 | 68 | 36.7 |
| 63 | 437 | 69 | 479 |
| 64 | <1 | 70 | 141 |
| 65 | 134 | 71 | 4.9 |
| 66 | 35.9 | 72 | 18.7 |

We claim:

1. A compound of Formula I aor the pharmaceutically acceptable acid addition salts thereof,

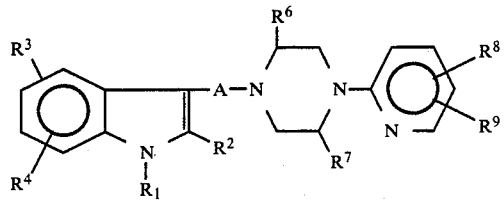

wherein
R$^1$ and R$^2$ are independently selected from hydrogen and lower alkyl, wherein lower means C$_{1-4}$;
R$^3$, R$^4$, R$^8$ and R$^9$ are independently selected from hydrogen, lower alkyl, lower alkoxy, carboxamide, halogen, trifluoromethyl and thio-lower alkyl, with the proviso that R$^8$ and R$^9$ cannot both be hydrogen at the same time;
A is a C$_{5-7}$ cycloalkanyl or cycloalkenyl ring, or A is

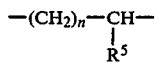

wherein n is an integer from 1 to 3 and $R^5$ is the same as $R^1$; and $R^6$ and $R^7$ are independently selected from hydrogen, methyl or $R^6$ and $R^7$ can be taken together as a methylene bridge.

2. The compound of claim 1 wherein A is a $C_{5-7}$ cycloalkanyl or cycloalkenyl ring.

3. The compound of claim 1 wherein A is

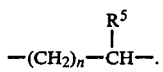

4. The compound of claim 1 wherein $R^6$ and $R^7$ are selected from hydrogen or methyl.

5. The compound of claim 1 wherein $R^6$ and $R^7$ are taken together as a methylene bridge.

6. The compound of claim 1; 1-[2-(1H-indol-3-yl)ethyl]-4(3-methoxy-2-pyridinyl)piperazine.

7. The compound of claim 1; 1-[2-(1H-indol-3-yl)ethyl]-4(3-trifluoromethyl-2-pyridinyl)-piperazine.

8. The compound of claim 1; 1-[2-(1H-indol-3-yl)ethyl]-4(3-methoxy-2-pyridinyl)-2-methypiperazine.

9. The compound of claim 1; 1-[2-(1H-indol-3-yl)ethyl]-5(3-methoxy-2-pyridinyl)-(1R,4R)-2,5-diazabicyclo[2.2.1] heptane.

10. The compound of claim 1; 1-[2-(1H-indol-3-yl)ethyl]-4(6-chloro-2-pyridinyl)piperazine.

11. The compound of claim 1; 1-[2-(1H-indol-3-yl)ethyl]-4(6-methoxy-2-pyridinyl)piperazine.

12. The compound of claim 1; 1-[2-(1H-indol-3-yl)ethyl]-5(3-methoxy-2-pyridinyl)-(1S,4S)-b 2,5-diazabicyclo[2.2.1] heptane.

13. The compound of claim 1; 1-[3-(1H-indol-3-yl)propyl]-4(3-methoxy-2-pyridinyl)piperazine.

14. The compound of claim 1; 1-[3-(1H-indol-3-yl)propyl]-4(6-chloro-2-pyridinyl)piperazine.

15. The compound of claim 1; 1-[4-(1H-indol-3-yl)butyl]-4(3-methoxy-2-pyridinyl)piperazine.

16. The compound of claim 1; 1-[2-(1H-indol-3-yl)ethyl]-4(6-trifluoromethyl-2-pyridinyl)-piperazine.

17. The compound of claim 1; 2-[2-(1H-indol-3-yl)ethyl]-5(6-chloro-2-pyridinyl)-(1S,4S)-2,5diazabicyclo[2.2.1]heptane.

18. The compound of claim 1; 2-[2-(1H-indol-3-yl)ethyl]-5(6-chloro-2-pyridinyl)-(1R,4R)-2,5-diazabicyclo[2.2.1] heptane.

19. The compound of claim 1; 1-[3-(1H-indol-3-yl)propyl]-4(6-trifluoromethyl-2-pyridinyl)-piperazine.

20. The compound of claim 1; 1-[4-(1H-indol-3-yl)butyl]-4(6-chloro-2-pyridinyl)piperazine.

21. The compound of claim 1; 1-[4-(1H-indol-3-yl)butyl]-4(6-trifluoromethyl-2-pyridinyl)-piperazine.

22. The compound of claim 1; 1-[3-(1H-indol-3-yl)propyl]-4(4-trifluoromethyl-2-pyridinyl)-piperazine.

23. The compound of claim 1; 2-[3-(1H-indol-3-yl)propyl]-5(3-methoxy-2-pyridinyl)-(1S,4)-2,5-diazabicyclo[2.2.1] heptane.

24. The compound of claim 1; 2-[3-(1H-indol-3-yl)propyl]-5(3-methoxy-2-pyridinyl)-(1R,4R)- 2,5-diazabicyclo[2.2.1] heptane.

25. The compound of claim 1; 1-[2-(1H-indol-3-yl)ethyl]-4(6-chloro-2-pyridinyl)-2-methylpiperazine.

26. The compound of claim 1; 1-[2-(1H-indol-3-yl)ethyl]-4(4-trifluoromethyl-2-pyridinyl)-piperazine.

27. The compound of claim 1; 1-[2-(5-methoxy-1H-indol-3-yl)ethyl]-4-(3-methoxy-2-pyridinyl)piperazine.

28. The compound of claim 1; 1-[2-(5-fluoro-1H-indol-3-yl)ethyl]-4-(3-methoxy-2-pyridinyl)piperazine.

29. The compound of claim 1; 1-[2-(5-methoxy-1H-indol-3-yl)ethyl]-4-(6-chloro-2-pyridinyl)piperazine.

30. The compound of claim 1; 1-[2-(5-fluoro-1H-indol-3-yl)ethyl]-4-(6-chloro-2-pyridinyl)piperazine.

31. The compound of claim 1; 1-[2-(1H-indol-3-yl)ethyl]-4(3-chloro-2-pyridinyl)piperazine.

32. The compound of claim 1; 1-[2-(5-fluoro-1H-indol-3-yl)ethyl]-4-(6-trifluoromethyl-2-pyridinyl)piperazine.

33. The compound of claim 1; 1-[2-(5-methoxy-1H-indol-3-yl)ethyl]-4-(6-trifluoromethyl-2-pyridinyl)piperazine.

34. The compound of claim 1; 3-[4-[4-(6-chloro-2-pyridinyl)1-piperazinyl]-1-cyclohexen-1-yl]-5-methoxyindole.

35. The compound of claim 1; 3-[4-[4-(6-chloro-2-pyridinyl)-1-piperazinyl]-1-cyclohexen-1-yl]-1H-indole.

36. The compound of claim 1; 3-[4-[4-(6-chloro-2-pyridinyl)1-piperazinyl]-1-cyclohexen-1-yl]-1H-indole-5-carboxamide.

37. The compound of claim 1; 1-[2-(N-methyl-1H-indol-3-yl)ethyl]-4-(3-methoxy-2-pyridinyl)-piperazine.

38. The compound of claim 1; 1-[2-(5,6-dimethoxy-1H-indol-3yl)ethyl]-4-(3-methoxy-2-pyridinyl)piperazine.

39. The compound of claim 1; 1-[3-(N-methyl-1H-indol-3-yl)propyl]-4-(3-methoxy-2-pyridinyl)-piperazine.

40. The compound of claim 1; 1-[3-(N-methyl-1H-indol-3-yl)propyl]-4-(6-chloro-2-pyridinyl)-piperazine.

41. The compound of claim 1; 1-[3-(5-fluoro-1H-indol-3-yl)propyl]-4-(6-chloro-2-pyridinyl)piperazine.

42. The compound of claim 1; 1-[3-(5-fluoro-1H-indol-3-yl)propyl]-4-(3-methoxy-2-pyridinyl)piperazine.

43. The compound of claim 1; 1-[2-(1H-indol-3-yl)ethyl]-4(5-chloro-2-pyridinyl)piperazine.

44. The compound of claim 1; 1-[2-[N-methyl-1H-indol-3-yl)ethyl]-4-(6-chloro-2-pyridinyl)-piperazine.

45. The compound of claim 1; 1-[2-(5-chloro-1H-indol-3-yl)ethyl]-4-(3-methoxy-2-pyridinyl)piperazine.

46. The compound of claim 1; 1-[2-(5-chloro-1H-indol-3-yl)ethyl]-4-(6-chloro-2-pyridinyl)piperazine.

47. The compound of claim 1; 1-[2-(5-chloro-1H-indol-3-yl)ethyl]-4-(6-trifluoromethyl-2-methyl-piperazine.

48. The compound of claim 1; 1-[2-(1H-indol-3-yl)ethyl]-4-(3-methoxy-2-pyridinyl)-2-methyl-piperazine.

49. The compound of claim 1; 4-(6-chloro-2-pyridinyl)-1-[2-(6-methoxy-1H-indol-3-yl)ethyl]-piperazine.

50. The compound of claim 1; 1- methoxy-1H-indol-3-yl)ethyl]-4-(3-methoxy-2-pyridinyl)-piperazine.

51. The compound of claim 1; 1-[3-(1H-indol-3-yl)-3-methylpropyl]-4-(6-chloro-2-pyridinyl)piperazine.

52. The compound of claim 1; 1-[3-(1H-indol-3-yl)-3-methylpropyl]-4-(3-methoxy-2-pyridiyl)piperazine.

53. The compound of claim 1; 1-[2-(5,6-dimethoxy-1H-indol3-yl)ethyl]-4-(6-trifluoromethyl-2-pyridinyl)-piperazine.

54. The compound of claim 1; 3-[4-[4-(6-chloro-2-pyridinyl)-1piperazinyl]-1-cyclohexen-1-yl]-5-fluoro-1H-indole.

55. The compound of claim 1; 4-(5-chloro-3-methoxy-2-pyridinyl)-1-[3-(1H-indol-3-yl)-propypyl]-piperazine hydrochloride.

56. The compound of claim 1; 4-(6-chloro-2-pyridinyl)-1-[3-(1H-indol-3-yl)propyl]-2-methyl-piperazine.

57. A method for ameliorating of depression in a mammal comprising administration to said mammal of an effective antidepressant amount of a compound claimed in claim 1.

58. A antidepressant pharmaceutical composition in dosage unit form suitable for systemic administration to a mammalian host comprising a pharmaceutical carrier and from about 1 to 500 mg of an active compound selected from the compounds claimed in claim 1.

* * * * *

UNITED STATES PATENT AND TRADEMARK OFFICE
CERTIFICATE OF CORRECTION

PATENT NO. : 4,954,502

DATED : 9/4/90

INVENTOR(S) : David W. Smith, Frand D. Yocca, Joseph P. Yevich, Ronald J. Mattson It is certified that error appears in the above—identified patent and that said Letters Patent is hereby corrected as shown below:

In Claim 1, column 39, line 66 - change "aor" to "or", column 42, line 45, hyphen missing between 4 and parenthetical name of pyridine moiety..

In Claim 6, column 41, line 23, do not separate "ethyl" as "e-thyl", column 41, line 24, hyphen missing between 4 and parenthetical name of pyridine moiety.

In Claim 7, column 41, line 25, do not separate "ethyl" as "e-thyl", column 41, line 26, hyphen missing between 4 and parenthetical name of pyridine moiety.

In Claim 8, column 41, line 27, do not separate "ethyl" as "e-thyl", column 41, line 28, hyphen missing between 4 and parenthetical name of pyridine moiety.

In Claim 9, column 41, line 29, do not separate "ethyl" as "e-thyl", column 41, line 30, hyphen missing between 5 and parenthetical name of pyridine moiety.

In Claim 10, column 41, line 32, do not separate "ethyl" as "e-thyl", in column 41, line 33, hyphen missing between 4 and parenthetical name of pyridine moiety.

In Claim 11, column 41, line 34, do not separate "ethyl" as "e-thyl", in column 41, line 35, hyphen missing between 4 and parenthetical name of pyridine moiety.

UNITED STATES PATENT AND TRADEMARK OFFICE
CERTIFICATE OF CORRECTION

PATENT NO. : 4,954,502

DATED : 9/4/90

INVENTOR(S) : David W. Smith, Frand D. Yocca, Joseph P. Yevich, Ronald J. Mattson It is certified that error appears in the above—identified patent and that said Letters Patent is hereby corrected as shown below:

In Claim 12, column 41, line 36, do not separate "ethyl" as "e-thyl", column 41, line 37, "(1S,4S-b 2,5" to "(1S,4S)-2,5", column 41, line 37, hyphen missing between 5 and parenthetical name of pyridine moiety.

In Claim 13, column 41, line 40, hyphen missing between 4 and parenthetical name of pyridine moiety.

In Claim 14, column 41, line 42, hyphen missing between 4 and parenthetical name of pyridine moiety.

In Claim 15, column 41, line 44, hyphen missing between 4 and parenthetical name of pyridine moiety.

In Claim 16, column 41, line 45, do not separate "ethyl" as "e-thyl", column 41, line 46, hyphen missing between 4 and parenthetical name of pyridine moiety.

In Claim 17, column 41, line 47, do not separate "ethyl" as "e-thyl", column 41, line 48, hyphen missing between 5 and parenthetical name of pyridine moiety.

In Claim 18, column 41, line 50, do not separate "ethyl" as "e-thyl", column 41, line 51, hyphen missing between 5 and parenthetical name of pyridine moiety.

In Claim 19, column 41, line 54, hyphen missing between 4 and parenthetical name of pyridine moiety.

In Claim 20, column 41, line 56, hyphen missing between 4 and parenthetical name of pyridine moiety.

UNITED STATES PATENT AND TRADEMARK OFFICE
CERTIFICATE OF CORRECTION

Page 3 of 4

PATENT NO. : 4,954,502
DATED : 9/4/90
INVENTOR(S) : David W. Smith, Frand D. Yocca, Joseph P. Yevich, Ronald J. Mattson It is certified that error appears in the above—identified patent and that said Letters Patent is hereby corrected as shown below:

In Claim 21, column 41, line 58, hyphen missing between 4 and parenthetical name of pyridine moiety.

In Claim 22, column 41, line 60, hyphen missing between 4 and parenthetical name of pyridine moiety.

In Claim 23, column 41, line 62, hyphen missing between 5 and parenthetical name of pyridine moiety, "(1S,4)" to "1S,4S)".

In Claim 24, column 41, line 65, hyphen missing between 5 and parenthetical name of pyridine moiety, "(1R,4R)-    2,5" to "(1R,4R) -2,5".

In Claim 25, column 41, line 67, do not separate "ethyl" as "e-thyl", column 41, line 68, hyphen missing between 4 and parenthetical name of pyridine moiety.

In Claim 26, column 42, line 1, do not separate "ethyl" as "e-thyl", column 42, line 2, hyphen missing between 4 and parenthetical name of pyridine moiety.

In Claim 29, column 42, line 8, change "-chIoro" to "chloro".

In Claim 31, column 42, line 12, hyphen missing between 4 and parenthetical name of pyridine moiety.

In Claim 43, column 42, line 44, do not separate "ethyl" as "e-thyl".

In Claim 47, column 42, line 53, change "-methyl-" to "-pyridinyl)".

UNITED STATES PATENT AND TRADEMARK OFFICE
CERTIFICATE OF CORRECTION

PATENT NO. : 4,954,502
DATED : 9/4/90
INVENTOR(S) : David W. Smith, Frand D. Yocca, Joseph P. Yevich, Ronald J. Mattson It is certified that error appears in the above—identified patent and that said Letters Patent is hereby corrected as shown below:

In Claim 48, column 42, line 56, do not separate "ethyl" as "e-thyl".

In Claim 50, column 42, line 60, change "1-methoxy" to "1-[5,6-dimethoxy".

In Claim 52, column 42, line 65, change "-pyridiyl" to pyridinyl".

In Claim 53, column 42, line 67, change "indol3-yl" to indol-3-yl".

In Claim 54, column 43, line 2, change "1piperazinyl" to "1-piperazinyl".

In Claim 55, column 43, line 5, change "propypyl" to propyl".

In Claim 57, column 44, line 1, delete "of".

In Claim 58, column 44, line 5, change "A" to "An".

Signed and Sealed this

Tenth Day of March, 1992

Attest:

HARRY F. MANBECK, JR.

Attesting Officer

Commissioner of Patents and Trademarks